(12) United States Patent
Kumar et al.

(10) Patent No.: US 11,473,095 B2
(45) Date of Patent: Oct. 18, 2022

(54) MODULATION OF TRANSGENE EXPRESSION IN PLANTS

(71) Applicant: CORTEVA AGRISCIENCE LLC, Indianapolis, IN (US)

(72) Inventors: Sandeep Kumar, Carmel, IN (US); Marcelo Ariel German, Lake Oswego, OR (US); Po-Hao Wang, Carmel, IN (US); Todd P. Glancy, Fairmount, IN (US); Shreedharan Sriram, Indianapolis, IN (US); Carla N. Yerkes, Crawfordsville, IN (US); Andrew J. Bowling, Zionsville, IN (US); Heather Pence, Indianapolis, IN (US); Andrew E. Robinson, Calvert City, KY (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

(21) Appl. No.: 16/856,536

(22) Filed: Apr. 23, 2020

(65) Prior Publication Data
US 2020/0248197 A1     Aug. 6, 2020

Related U.S. Application Data

(62) Division of application No. 15/705,312, filed on Sep. 15, 2017, now abandoned.

(60) Provisional application No. 62/406,560, filed on Oct. 11, 2016.

(51) Int. Cl.
*C12N 15/82* (2006.01)

(52) U.S. Cl.
CPC ..... *C12N 15/8218* (2013.01); *C12N 15/8223* (2013.01); *C12N 15/8234* (2013.01); *C12N 15/8274* (2013.01)

(58) Field of Classification Search
None
See application file for complete search history.

(56) References Cited

U.S. PATENT DOCUMENTS

| | | | |
|---|---|---|---|
| 7,723,568 | B2 | 5/2010 | Monsanto |
| 8,685,677 | B2 | 4/2014 | Novak |
| 9,670,502 | B2 | 6/2017 | Huang |
| 2002/0002201 | A1 | 2/2002 | Curiel et al. |
| 2004/0268441 | A1 | 12/2004 | Vance et al. |
| 2006/0174380 | A1 | 8/2006 | Carrington |
| 2006/0185027 | A1 | 8/2006 | Bartel |
| 2006/0200878 | A1 | 9/2006 | Lutfiyya |
| 2007/0089196 | A1* | 4/2007 | Huang ............... C12N 15/8217 800/278 |
| 2010/0257621 | A1 | 10/2010 | Ketkar et al. |
| 2014/0007295 | A1 | 1/2014 | Huang |
| 2014/0356961 | A1* | 12/2014 | Meyers ............... C12N 15/8279 435/468 |
| 2015/0144669 | A1 | 5/2015 | Chang et al. |

FOREIGN PATENT DOCUMENTS

| | | |
|---|---|---|
| CN | 101466837 | 6/2009 |
| CN | 103740725 | 4/2014 |
| CN | 105325288 | 2/2016 |
| NZ | 260511 | 7/1995 |
| WO | 1998/44138 | 10/1998 |
| WO | 2000/77223 | 12/2000 |
| WO | 2003/093441 A2 | 11/2003 |
| WO | 2004/009779 | 1/2004 |
| WO | 2005/035769 A2 | 4/2005 |
| WO | 2006/073727 A2 | 7/2006 |
| WO | 2006/074400 A2 | 7/2006 |
| WO | 2006/138638 A2 | 12/2006 |
| WO | 2007/047016 A2 | 4/2007 |

OTHER PUBLICATIONS

Li et al 2010 Plant Physiology 153:1759-1770 (Year: 2010).*
Li et al., 2010 Plant Physiology 153:1759-1770 (2010).
Parizotto et al., Genes and Development (2004) 18:2237-2242.
Mansfield, J. H., et al., "MicroRNA-responsive 'sensor' transgenes uncover Hox-like and other developmentally regulated patterns of vertebrate microRNA expression", Nature Genetics, 2004, vol. 36, No. 10, pp. 1079-1083.
Stark, A., et al., "Identification of *Drosophila* microRNA targets", PLOS Biology, 2003, vol. 1, Issue 3, pp. 397-409.
Brennecke, J., et al., "bantam encodes a developmentally regulated microRNA that controls cell proliferation and regulates the proapoptotic gene hid in *Drosophila*", Cell, 2003, vol. 113, pp. 25-36.
Laufs, P., et al., "MicroRNA regulation of the CUC genes is required for boundary size control in *Arabidopsis meristems*", Development, 2004, vol. 131, No. 17, pp. 4311-4322.
Palatnik, J. F., et al., "Control of leaf morphogenesis by microRNAs", Nature, 2003, vol. 425, pp. 257-263.
MALLORYb, A. C., et al., "MicroRNA regulation of NAC-domain targets is required for proper formation and separation of adjacent embryonic, vegetative, and floral organs", Current Biology, 2004, vol. 14, pp. 1035-1046.
Chen, X., "A microRNA as a translational repressor of APETALA2 in *Arabidopsis* flower development", Science, 2004, vol. 303, pp. 2022-2025.
Zeng, Y., et al., "Both natural and designed micro RNAs can inhibit the expression of cognate mRNAs when expressed in human cells", Molecular Cell, 2002, vol. 9, pp. 1327-1333.
Lim, L. P., et al., "Microarray analysis shows that some microRNAs downregulate large numbers of target mRNAs", Nature, 2005, vol. 433, pp. 769-773.
Berger, E. M., et al., "Inhibition of micro-RNA-induced RNA silencing by 2.-0-methyl oligonucleotides in *Drosophila* S2 cells", In Vitro Cell. Dev. Biol.—Animal, 2005, vol. 41, pp. 12-18.

(Continued)

*Primary Examiner* — Brent T Page

(57) ABSTRACT

This disclosure concerns the use of endogenous plant RNAi machinery to preferentially or specifically reduce transgene expression. In some embodiments, the disclosure concerns specific reduction of transgene expression in seed tissues of a dicot plant.

29 Claims, 10 Drawing Sheets

Specification includes a Sequence Listing.

(56) References Cited

OTHER PUBLICATIONS

Carrington, J. C., et al., "Role of microRNAs in plant and animal development", Science, 2003, vol. 301, pp. 336-338.
He, L., et al., "MicroRNAs: small RNAs with a big role in gene regulation", Nature Reviews, 2004, vol. 5, pp. 522-531.
Bartel, D. P., et al., "Micromanagers of gene expression: the potentially widespread influence of metazoan microRNAs", Nature Review, 2004, vol. 5, pp. 396-400.
Brown, B. D., et al., "Endogenous microRNA regulation suppresses transgene expression in hematopoietic lineages and enables stable gene transfer", Nature Medicine, 2006, vol. 12, No. 5, pp. 585-591.
Vance, V., et al., "RNA silencing in plants—defense and counterdefense", Science, 2001, vol. 292, pp. 2277-2280.
Zamore, P. D., "RNA interference: listening to the sound of silence", Nature Structural Biology, 2001, vol. 8, No. 9, pp. 746-749.
Lee, R. C., et al., "An extensive class of small RNAs in Caenorhabditis elegans", Science, 2001, vol. 294, pp. 862-864.
Mallory, A. C., et al., "MicroRNA control of PHABULOSA in leaf development: importance of pairing to the microRNA 5' region", The EMBO Journal, 2004, vol. 23, pp. 3356-3364.
Doench, J. G., et al., "Specificity of microRNA target selection in translational repression", Genes & Development, 2004, vol. 18, pp. 504-511.
Mcmanus, M. T., et al., "Gene silencing using micro-RNA designed hairpins", RNA, 2002, vol. 8, pp. 842-850.
Juarez, M. T., et al., "MicroRNA-mediated repression of rolled leaf1 specifies maize leaf polarity", Nature, 2004, vol. 428, pp. 84-88.
Kidner, C. A., et al., "Spatially restricted microRNA directs leaf polarity through ARGONAUTE1", Nature, 2004, vol. 428, pp. 81-84.
Jones-Rhoades, M. W., et al., "Computational identification of plant microRNAs and their targets, including a stress-induced miRNA", Molecular Cell, 2004, vol. 14, pp. 787-799.
Sunkar, R., et al., "Novel and stress-regulated microRNAs and other small RNAs from *Arabidopsis*", The Plant Cell, 2004, vol. 16, pp. 2001-2019.
Yekta, S., et al., "MicroRNA-directed cleavage of HOXB8 mRNA", Science, 2004, vol. 304, pp. 594-596.
Sempere, L. F., et al., "Expression profiling of mammalian microRNAs uncovers a subset of brain-expressed microRNAs with pos murine and human neuronal differentiation", Genome Biology, 2004, vol. 5, R.13.
Opperman, C. H., et al., "Root-knot nematode-directed expression of a plant root-specific gene", Science, 1994, vol. 263, pp. 221-223.
Lagos-Quintana, M., et al., "Identification of novel genes coding for small expressed RNAs", Science, 2001, vol. 294, pp. 853-858.
Lagos-Quintana, M., et al., "Identification of tissue-specific microRNAs from mouse", Current Biology, 2002, vol. 12, pp. 735-739.
Lim, L. P., et al., "Vertebrate microRNA genes", Science, 2003, vol. 299, p. 1540.
Mourelatos, Z., et al., "miRNPs: a novel class of ribonucleoproteins containing numerous microRNAs", Genes & Development, 2002, vol. 16, pp. 720-728.
Dostie, J., et al., "Numerous microRNPs in neuronal cells containing novel microRNAs", RNA, 2003, vol. 9, pp. 180-186.
Park, W., et al., "Carpel Factory, a Dicer Homolog, and HEN1, a Novel Protein, Act in microRNA Metabolism in *Arabidopsis thaliana*", Current Biology, 2002, vol. 12, pp. 1484-1495.
Himber, C., et al., "Transitivity-Dependent and -Independent Cell-to-Cell Movement of RNA Silencing", The EMBO Journal, 2003, vol. 22, No. 17, pp. 4523-4533.
Llave, C., et al., "Cleavage of Scarecrow-Like mRNA Targets Directed by a Class of *Arabidopsis* miRNA", Science, 2002, vol. 297, pp. 2053-2056.
Miki, D., et al., "RNA Silencing of Single and Multiple Members in a Gene Family of Rice", Plant Physiology, 2005, vol. 138, pp. 1903-1913.
Mallory, A. C., et al., "MicroRNA-Directed Regulation of *Arabidopsis* Auxin Response FACTOR17 Is Essential for Proper Development and Modulates Expression of Early Auxin Response Genes", Plant Cell, 2005, vol. 17, No. 5, pp. 1360-1375.
Tuteja, J. H., et al. "Endogenous, tissue-specific short interfering RNAs silence the chalcone synthase gene family in Glycine max seed coats." The Plant Cell 21.10 (2009): 3063-3077.
Dugas, D. V., and Bartel, B. "MicroRNA regulation of gene expression in plants." Current opinion in plant biology 7.5 (2004): 512-520.
Kulcheski F. R., et al. "Identification of novel soybean microRNAs involved in abiotic and biotic stresses." BMC genomics 12.1 (2011): 307.
Song, Q., et al. "Identification of miRNAs and their target genes in developing soybean seeds by deep sequencing." BMC plant biology 11.1 (2011): 5.
Wong, C. E., et al. "MicroRNAs in the shoot apical meristem of soybean." Journal of experimental botany 62.8 (2011): 2495-2506.
Zhang, L., et al. "A genome-wide characterization of microRNA genes in maize." PLoS genetics 5.11 (2009): e1000716.
Written Opinion of the ISR. dated Dec. 15, 2017 for PCT/US2017/0519691.
Luo, Z., et al. "MiR1511 co-regulates with miR1511* to cleave the GmRPL4a gene in soybean." Chinese Science Bulletin 57.28 (2012): 3804-3810.
Paul, S., et al. "Identification and expression profiling of Vigna mungo microRNAs from leaf small RNA transcriptome by deep sequencing." Journal of integrative plant biology 56.1 (2014): 15-23.

* cited by examiner

SEQUENCE LISTING

```
<160> NUMBER OF SEQ ID NOS: 23

<210> SEQ ID NO 1
<211> LENGTH: 21
<212> TYPE: RNA
<213> ORGANISM: Glycine max

<400> SEQUENCE: 1
ugagaccaaa ugagcagcug a                                              21

<210> SEQ ID NO 2
<211> LENGTH: 21
<212> TYPE: DNA
<213> ORGANISM: Artificial Sequence
<220> FEATURE:
<223> OTHER INFORMATION: target site HTRNA15975.1

<400> SEQUENCE: 2
tcagctgctc atttggtctc a                                              21

<210> SEQ ID NO 3
<211> LENGTH: 22
<212> TYPE: RNA
<213> ORGANISM: Glycine max

<400> SEQUENCE: 3
uaacugaaca uucuuagagc au                                             22

<210> SEQ ID NO 4
<211> LENGTH: 22
<212> TYPE: DNA
<213> ORGANISM: Artificial Sequence
<220> FEATURE:
<223> OTHER INFORMATION: target site HTRNA15976.1

<400> SEQUENCE: 4
atgctctaag aatgttcagt ta                                             22
```

<210> SEQ ID NO 5
<211> LENGTH: 1441
<212> TYPE: DNA
<213> ORGANISM: Artificial Sequence
<220> FEATURE:
<223> OTHER INFORMATION: expression cassette

<400> SEQUENCE: 5

| | |
|---|---|
| atggctcaga ccactctcca aatcacaccc actggtgcca ccttgggtgc cacagtcact | 60 |
| ggtgttcacc ttgccacact tgacgatgct ggtttcgctg ccctccatgc agcctggctt | 120 |
| caacatgcac tcttgatctt ccctgggcaa cacctcagca atgaccaaca gattaccttt | 180 |
| gctaaacgct ttggagcaat tgagaggatt ggcggaggtg acattgttgc catatccaat | 240 |
| gtcaaggcag atggcacagt cgccagcac tctcctgctg agtgggatga catgatgaag | 300 |
| gtcattgtgg gcaacatggc ctggcacgcc gactcaacct acatgccagt catggctcaa | 360 |
| ggagctgtgt tcagcgcaga agttgtccca gcagttgggg cagaacctg ctttgctgac | 420 |
| atgagggcag cctacgatgc ccttgatgag caacccgtg ctcttgttca ccaaaggtct | 480 |
| gctcgtcact cccttgtgta ttctcagagc aagttgggac atgtccaaca ggccgggtca | 540 |
| gcctacatag gttatggcat ggacaccact gcaactcctc tcagaccatt ggtcaaggtg | 600 |
| catcctgaga ctggaaggcc cagcctcttg atcggccgcc atgccatgc catccctggc | 660 |
| atggatgcag ctgaatcaga gcgcttcctt gaaggacttg ttgactgggc ctgccaggct | 720 |
| cccagagtcc atgctcacca atgggctgct ggagatgtgg ttgtgtggga caaccgctgt | 780 |
| ttgctccacc gtgctgagcc ctgggatttc aagttgccac gtgtgatgtg gcactccaga | 840 |
| ctcgctggac gcccagaaac tgagggtgct gccttggttt gagtagttag cttaatcacc | 900 |
| tagagctcgg tcaccagcat aattttatt aatgtactaa attactgttt tgttaaatgc | 960 |
| aattttgctt tctcgggatt ttaatatcaa aatctattta gaaatacaca atattttgtt | 1020 |
| gcaggcttgc tggagaatcg atctgctatc ataaaaatta caaaaaaatt ttatttgcct | 1080 |
| caattatttt aggattggta ttaaggacgc ttaaattatt tgtcgggtca ctacgcatca | 1140 |
| ttgtgattga agatcagc gatacgaaat attcgtagta ctatcgataa tttatttgaa | 1200 |
| aattcataag aaaagcaaac gttacatgaa ttgatgaaac aatacaaaga cagataaagc | 1260 |
| cacgcacatt taggatattg gccgagatta ctgaatattg agtaagatca cggaatttct | 1320 |
| gacaggagca tgtcttcaat tcagcccaaa tggcagttga aatactcaaa ccgccccata | 1380 |
| tgcaggagcg gatcattcat tgtttgtttg gttgcctttg ccaacatggg agtccaaggt | 1440 |
| t | 1441 |

<210> SEQ ID NO 6
<211> LENGTH: 1462
<212> TYPE: DNA
<213> ORGANISM: Artificial Sequence
<220> FEATURE:
<223> OTHER INFORMATION: expression cassette

<400> SEQUENCE: 6

| | |
|---|---|
| atggctcaga ccactctcca aatcacaccc actggtgcca ccttgggtgc cacagtcact | 60 |
| ggtgttcacc ttgccacact tgacgatgct ggtttcgctg ccctccatgc agcctggctt | 120 |
| caacatgcac tcttgatctt ccctgggcaa cacctcagca atgaccaaca gattaccttt | 180 |
| gctaaacgct ttggagcaat tgagaggatt ggcggaggtg acattgttgc catatccaat | 240 |

```
gtcaaggcag atggcacagt gcgccagcac tctcctgctg agtgggatga catgatgaag      300
gtcattgtgg gcaacatggc ctggcacgcc gactcaacct acatgccagt catggctcaa      360
ggagctgtgt tcagcgcaga agttgtccca gcagttgggg gcagaacctg ctttgctgac      420
atgagggcag cctacgatgc ccttgatgag caacccgtg ctcttgttca ccaaaggtct       480
gctcgtcact cccttgtgta ttctcagagc aagttgggac atgtccaaca ggccgggtca      540
gcctacatag gttatggcat ggacaccact gcaactcctc tcagaccatt ggtcaaggtg      600
catcctgaga ctggaaggcc cagcctcttg atcggccgcc atgcccatgc catccctggc      660
atggatgcag ctgaatcaga gcgcttcctt aaggacttg ttgactgggc tgccaggct        720 cccagagtcc atgctcacca tgggctgct ggagatgtgg ttgtgtggga caaccgctgt       780
ttgctccacc gtgctgagcc ctgggatttc aagttgccac gtgtgatgtg gcactccaga      840
ctcgctggac gcccagaaac tgagggtgct gccttggttt gagtagttag cttaatcacc      900
tagagctcgg tcagctgctc atttggtctc atcaccagca taatttttat taatgtacta     960
aattactgtt ttgttaaatg caattttgct ttctcgggat tttaatatca aaatctattt     1020
agaaatacac aatattttgt tgcaggcttg ctggagaatc gatctgctat cataaaaatt     1080
acaaaaaaat tttatttgcc tcaattattt taggattggt attaaggacg cttaaattat     1140
ttgtcgggtc actacgcatc attgtgattg agaagatcag cgatacgaaa tattcgtagt     1200
actatcgata atttatttga aaattcataa gaaaagcaaa cgttacatga attgatgaaa     1260
caatacaaag acagataaag ccacgcacat ttaggatatt ggccgagatt actgaatatt     1320
gagtaagatc acggaatttc tgacaggagc atgtcttcaa ttcagcccaa atggcagttg     1380
aaatactcaa accgccccat atgcaggagc ggatcattca ttgtttgttt ggttgccttt     1440
gccaacatgg gagtccaagg tt                                              1462
```

<210> SEQ ID NO 7
<211> LENGTH: 1463
<212> TYPE: DNA
<213> ORGANISM: Artificial Sequence
<220> FEATURE:
<223> OTHER INFORMATION: expression cassette

<400> SEQUENCE: 7

```
atggctcaga ccactctcca aatcacaccc actggtgcca ccttgggtgc cacagtcact       60
ggtgttcacc ttgccacact tgacgatgct ggtttcgctg ccctccatgc agcctggctt      120
caacatgcac tcttgatctt ccctgggcaa cacctcagca tgaccaaca gattacccttt      180 gctaaacgct ttggagcaat tgagaggatt ggcggaggtg acattgttgc catatccaat      240
gtcaaggcag atggcacagt gcgccagcac tctcctgctg agtgggatga catgatgaag      300
gtcattgtgg gcaacatggc ctggcacgcc gactcaacct acatgccagt catggctcaa      360
ggagctgtgt tcagcgcaga agttgtccca gcagttgggg gcagaacctg ctttgctgac      420
atgagggcag cctacgatgc ccttgatgag caacccgtg ctcttgttca ccaaaggtct       480
gctcgtcact cccttgtgta ttctcagagc aagttgggac atgtccaaca ggccgggtca      540
gcctacatag gttatggcat ggacaccact gcaactcctc tcagaccatt ggtcaaggtg      600
catcctgaga ctggaaggcc cagcctcttg atcggccgcc atgcccatgc catccctggc      660
atggatgcag ctgaatcaga gcgcttcctt aaggacttg ttgactgggc tgccaggct        720 cccagagtcc atgctcacca tgggctgct ggagatgtgg ttgtgtggga caaccgctgt       780
ttgctccacc gtgctgagcc ctgggatttc aagttgccac gtgtgatgtg gcactccaga      840
```

```
ctcgctggac gcccagaaac tgagggtgct gccttggttt gagtagttag cttaatcacc      900
tagagctcgg atgctctaag aatgttcagt tatcaccagc ataattttta ttaatgtact      960
aaattactgt tttgttaaat gcaattttgc tttctcggga ttttaatatc aaaatctatt     1020
tagaaataca caatattttg ttgcaggctt gctggagaat cgatctgcta tcataaaaat     1080
tacaaaaaaa ttttatttgc ctcaattatt ttaggattgg tattaaggac gcttaaatta     1140
tttgtcgggt cactacgcat cattgtgatt gagaagatca gcgatacgaa atattcgtag     1200
tactatcgat aatttatttg aaaattcata agaaagcaa acgttacatg aattgatgaa     1260
acaatacaaa gacagataaa gccacgcaca tttaggatat tggccgagat tactgaatat     1320
tgagtaagat cacggaattt ctgacaggag catgtcttca attcagccca aatggcagtt     1380
gaaatactca aaccgcccca tatgcaggag cggatcattc attgtttgtt tggttgcctt     1440
tgccaacatg ggagtccaag gtt                                             1463

<210> SEQ ID NO 8
<211> LENGTH: 1322
<212> TYPE: DNA
<213> ORGANISM: Arabidopsis thaliana

<400> SEQUENCE: 8
gtcgacctgc aggtcaacgg atcaggatat tcttgtttaa gatgttgaac tctatggagg       60
tttgtatgaa ctgatgatct aggaccggat aagttcccct cttcatagcg aacttattca      120
aagaatgttt tgtgtatcat tcttgttaca ttgttattaa tgaaaaaata ttattggtca      180
ttggactgaa cacgagtgtt aaatatggac caggccccaa ataagatcca ttgatatatg      240
aattaaataa caagaataaa tcgagtcacc aaaccacttg cctttttaa cgagacttgt      300 tcaccaactt gatacaaaag tcattatcct atgcaaatca ataatcatac aaaaatatcc      360
aataacacta aaaattaaa agaaatggat aatttcacaa tatgttatac gataaagaag      420
ttacttttcc aagaaattca ctgattttat aagcccactt gcattagata aatggcaaaa      480
aaaaacaaaa aggaaaagaa ataaagcacg aagaattcta gaaaatacga aatacgcttc      540
aatgcagtgg gacccacggt tcaattattg ccaattttca gctccaccgt atatttaaaa      600
aataaaacga taatgctaaa aaaatataaa tcgtaacgat cgttaaatct caacggctgg      660
atcttatgac gaccgttaga aattgtggtt gtcgacgagt cagtaataaa cggcgtcaaa      720
gtggttgcag ccggcacaca cgagtcgtgt ttatcaactc aaagcacaaa tactttttcct      780 caacctaaaa ataaggcaat tagccaaaaa caactttgcg tgtaaacaac gctcaataca      840
cgtgtcattt tattattagc tattgcttca ccgccttagc tttctcgtga cctagtcgtc      900
ctcgtctttt cttcttcttc ttctataaaa caatacccaa agcttcttct tcacaattca      960
gatttcaatt tctcaaaatc ttaaaaactt tctctcaatt ctctctaccg tgatcaaggt     1020
aaatttctgt gttccttatt ctctcaaaat cttcgatttt gttttcgttc gatcccaatt     1080
tcgtatatgt tctttggttt agattctgtt aatcttagat cgaagacgat tttctgggtt     1140
tgatcgttag atatcatctt aattctcgat tagggtttca taaatatcat ccgatttgtt     1200
caaataattt gagttttgtc gaataattac tcttcgattt gtgatttcta tctagatctg     1260
gtgttagttt ctagtttgtg cgatcgaatt tgtcgattaa tctgagtttt tctgattaac     1320
ag                                                                    1322

<210> SEQ ID NO 9
```

-continued

```
<211> LENGTH: 17
<212> TYPE: DNA
<213> ORGANISM: Artificial Sequence
<220> FEATURE:
<223> OTHER INFORMATION: primer oligonucleotide

<400> SEQUENCE: 9
aacccgtgct cttgttc                                                    17

<210> SEQ ID NO 10
<211> LENGTH: 18
<212> TYPE: DNA
<213> ORGANISM: Artificial Sequence
<220> FEATURE:
<223> OTHER INFORMATION: primer oligonucleotide

<400> SEQUENCE: 10
ggatgcacct tgaccaat                                                   18

<210> SEQ ID NO 11
<211> LENGTH: 16
<212> TYPE: DNA
<213> ORGANISM: Artificial Sequence
<220> FEATURE:
<223> OTHER INFORMATION: probe oligonucleotide

<400> SEQUENCE: 11
caggccgggt cagcct                                                     16

<210> SEQ ID NO 12
<211> LENGTH: 29
<212> TYPE: DNA
<213> ORGANISM: Artificial Sequence
<220> FEATURE:
<223> OTHER INFORMATION: primer oligonucleotide

<400> SEQUENCE: 12
acaagagtgg attgatgatc tagagaggt                                       29

<210> SEQ ID NO 13
<211> LENGTH: 29
<212> TYPE: DNA
<213> ORGANISM: Artificial Sequence
<220> FEATURE:
<223> OTHER INFORMATION: primer oligonucleotide

<400> SEQUENCE: 13
ctttgatgcc tatgtgacac gtaaacagt                                       29

<210> SEQ ID NO 14
<211> LENGTH: 29
<212> TYPE: DNA
<213> ORGANISM: Artificial Sequence
<220> FEATURE:
<223> OTHER INFORMATION: probe oligonucleotide

<400> SEQUENCE: 14
ggtgttgtgg ctggtattgc ttacgctgg                                       29

<210> SEQ ID NO 15
<211> LENGTH: 21
<212> TYPE: DNA
<213> ORGANISM: Artificial Sequence
<220> FEATURE:
<223> OTHER INFORMATION: primer oligonucleotide

<400> SEQUENCE: 15
```
cgccgaagta tcgactcaac t            21

<210> SEQ ID NO 16
<211> LENGTH: 19
<212> TYPE: DNA
<213> ORGANISM: Artificial Sequence
<220> FEATURE:
<223> OTHER INFORMATION: primer oligonucleotide

<400> SEQUENCE: 16
gcaacgtcgg ttcgagatg            19

<210> SEQ ID NO 17
<211> LENGTH: 24
<212> TYPE: DNA
<213> ORGANISM: Artificial Sequence
<220> FEATURE:
<223> OTHER INFORMATION: probe oligonucleotide

<400> SEQUENCE: 17
tcagaggtag ttggcgtcat cgag            24

<210> SEQ ID NO 18
<211> LENGTH: 24
<212> TYPE: DNA
<213> ORGANISM: Artificial Sequence
<220> FEATURE:
<223> OTHER INFORMATION: primer oligonucleotide

<400> SEQUENCE: 18
gtaatatggg ctcagaggaa tggt            24

<210> SEQ ID NO 19
<211> LENGTH: 23
<212> TYPE: DNA
<213> ORGANISM: Artificial Sequence
<220> FEATURE:
<223> OTHER INFORMATION: primer oligonucleotide

<400> SEQUENCE: 19
atggagaaga acattggaat tgc            23

<210> SEQ ID NO 20
<211> LENGTH: 23
<212> TYPE: DNA
<213> ORGANISM: Artificial Sequence
<220> FEATURE:
<223> OTHER INFORMATION: probe oligonucleotide

<400> SEQUENCE: 20
ccatggcccg gtaccatctg gtc            23

<210> SEQ ID NO 21
<211> LENGTH: 23
<212> TYPE: DNA
<213> ORGANISM: Artificial Sequence
<220> FEATURE:
<223> OTHER INFORMATION: primer oligonucleotide

<400> SEQUENCE: 21
gtgactcaca ccatcaccag agt            23

<210> SEQ ID NO 22
<211> LENGTH: 23
<212> TYPE: DNA

```
<213> ORGANISM: Artificial Sequence
<220> FEATURE:
<223> OTHER INFORMATION: primer oligonucleotide

<400> SEQUENCE: 22
atccaggctg tcctctccct ata                                              23

<210> SEQ ID NO 23
<211> LENGTH: 19
<212> TYPE: DNA
<213> ORGANISM: Artificial Sequence
<220> FEATURE:
<223> OTHER INFORMATION: probe oligonucleotide

<400> SEQUENCE: 23
caataccagt tgtgcgacc                                                   19
```

MODULATION OF TRANSGENE EXPRESSION IN PLANTS

CROSS REFERENCE TO RELATED APPLICATION

The present application is a divisional application of U.S. patent application Ser. No. 15/705,312 filed Sep. 15, 2017, which claims priority to the benefit of U.S. Provisional Patent Application Ser. No. 62/406,560 filed Oct. 11, 2016 the disclosure of which is hereby incorporated by reference in its entirety.

FIELD OF THE DISCLOSURE

The present disclosure relates to polynucleotides, constructs and methods for the control of transgene expression in plants. Specific embodiments herein relate to constructs and methods for utilizing the native RNA interference (RNAi) machinery of a plant cell to effect tissue-specific expression of a gene of interest, for example, in seed or root tissues.

BACKGROUND

RNA interference (RNAi) is a process utilizing endogenous cellular pathways, whereby an interfering RNA (iRNA) molecule (e.g., a dsRNA molecule) that is specific for a target gene sequence results in the reduced expression (e.g., by degradation) of the mRNA encoded thereby. In recent years, RNAi has been used to perform gene "knockdown" (i.e., downregulation or inhibition of expression) in a number of species and experimental systems; for example, *C. elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short double-stranded fragments of approximately 20-24 nucleotides. The inhibitory double-stranded RNA is unwound into two single-stranded RNAs: the passenger strand and the guide strand. The passenger strand is degraded, and the guide strand is incorporated into the RNA-induced silencing complex (RISC). Post-transcriptional gene silencing (translational repression) occurs when the guide strand binds specifically to a complementary sequence of an mRNA molecule and induces cleavage by Argonaute, the catalytic component of the RISC complex.

Plant micro-RNAs (miRNAs) are typically produced from fold-back structures having a partial double-stranded structure (e.g., "hairpins"), and usually are nearly perfectly complementary with "target sites," which are found most commonly in protein-coding regions of the genome. As a result, plant miRNAs function generally to guide mRNA cleavage. Watson et al. (2005) FEBS Lett. 579:5982-7. In contrast, animal miRNAs contain relatively low levels of complementarity to their target sites, and thus generally do not guide cleavage, but rather function to repress expression at the translational or co-translational level. Watson et al. (2005), supra; Tomari and Zamore (2005) Genes Dev. 19(5): 517-29. Although miRNA sequences are not conserved between plants and animals, the RNAi pathways that utilize these genes are highly similar. Millar and Waterhouse (2005) Funct. Integr. Genomics 5:129-35. For example, while the biogenesis of miRNAs in plants is accomplished by a different set of related enzymes than accomplish the biogenesis of animal miRNAs, the miRNA molecules themselves have a characteristic structure that is capable of effecting mRNA cleavage or translational repression, depending on their degree of sequence complementarity to the target gene.

In addition to miRNAs, plants also produce endogenous 21-25 nucleotide small inhibitory-RNAs (siRNAs). Most of these differ from miRNAs, in that they arise from double-stranded RNA (rather than imperfect fold-back structures), which in some cases are generated by the activity of RNA-Dependent RNA Polymerases (RDRs).

Most plants contain four DICER-LIKE (DCL) proteins, one of which (DCL1) is necessary for maturation of most miRNA precursors. Kurihara and Watanabe (2004) Proc. Natl. Acad. Sci. USA 101:12753-8. Animal miRNA precursor processing requires the sequential nucleolytic activity of DROSHA and DICER. Lee et al. (2003) Nature 425:415-9. In animals, Exportin-5 (ExpS) regulates the transport of pre-miRNAs from the nucleus to the cytoplasm. Bohnsack et al. (2004) RNA 10:185-91.

Only RNA transcripts complementary to the siRNA and/or miRNA are cleaved and degraded by RNAi, and thus the knock-down of mRNA expression is sequence-specific. The gene silencing effect of RNAi persists for days and, under experimental conditions, can lead to a decline in abundance of the targeted transcript of 90% or more, with consequent reduction in levels of the corresponding protein.

BRIEF SUMMARY OF THE DISCLOSURE

Described herein are the compositions and methods directed to a novel plant small RNA (sRNA)-mediated approach for modulation of transgene expression in plants. The approach utilizes sRNAs (e.g., endogenous siRNAs and miRNAs) that are expressed in specific tissues, preferred tissues, or cell types for targeted repression or knockdown of (trans) gene expression. In some embodiments, a target site of an sRNA is fused within a transgene expression cassette sequence that expresses an agronomic trait gene, an insect resistance gene, an herbicide tolerance gene, a non-coding RNA gene, or a selectable marker gene. Tissue-specific expression of sRNA (e.g., endogenous sRNAs) in the tissue results in downregulation of the transgene, which results in selective expression of the transgene only in desired tissues. In some embodiments where the transgene is a herbicide tolerance gene, downregulation of the transgene confers sensitivity to the herbicide upon the specific tissue, while other plant tissues where the sRNA is not expressed remain tolerant.

In some embodiments, sRNAs are specifically expressed in pollen, ovule, cotyledon, hypocotyl, anther, pistil, pod, flower, shoot or stalk tissue of a plant, and in particular embodiments in leaf, root or seed tissue of a plant, so as to repress/knockdown the expression of a transgene in these specific tissues. Particular embodiments include the sRNA-mediated tissue-specific expression of any transgene in plants. In examples, the transgene is an herbicide tolerance gene. In some embodiments, sRNAs are specifically or preferentially expressed in, for example, the root or seed tissue of a plant, so as to specifically or preferentially reduce expression of a transgene in the tissue.

Described herein are nucleic acid expression constructs, which constructs comprise a gene of interest, a plant promoter operably linked to the gene of interest, and a target site for at least one sRNA molecule. In embodiments, RNA may be transcribed from the gene of interest in vivo when the construct is introduced into a plant cell, which RNA is then degraded by an RNAi mechanism under the control of the sRNA molecule(s) only in tissues or at times where/when the sRNA is also expressed. In particular embodiments, the gene of interest is an agronomic trait gene (e.g., nitrogen use efficiency gene, water use efficiency gene, or nutritional quality gene (e.g., modified oil profile)), an herbicide tolerance gene, an insect resistance gene, or a selectable marker gene. In particular embodiments, the internal sRNA targeting site is, for example, 20-25 nucleotides in length. In certain embodiments, the sRNA is miR1512 or miR3522. Further, in certain embodiments, the target site is SEQ ID NO:2, SEQ ID NO:4, or combinations thereof.

Also described herein are transgenic plant cells, plant tissues, and plants comprising at least one of the foregoing nucleic acid expression constructs. In particular embodiments, the sRNA molecule is differentially expressed in different plant cells and tissues. For example, the gene (e.g., transgene) encoding the sRNA molecule may be operably linked to a non-constitutive promoter (e.g., a tissue-specific promoter). In particular embodiments, the sRNA is an endogenous sRNA of the plant cell. In certain examples, the sRNA is an endogenous sRNA that is expressed predominantly in certain tissues (e.g., pollen, ovule, cotyledon, hypocotyl, anther, pistil, pod, flower, shoot, stalk, root, leaf, or seed tissues), which sRNA directs degradation specifically in these tissues of RNA transcribed from the gene of interest, wherein the expression of RNA transcribed from the gene of interest in other tissues is essentially unaffected. Also described herein are methods of producing the transgenic plant cells by transforming plant cells with the nucleic acid expression cassettes disclosed herein.

Further described herein are methods for reducing expression of a gene of interest in a plant by growing a plant comprising the nucleic acid expression cassettes described herein and comprising a gene of interest and a sRNA target site. In such methods, expression of the gene of interest is downregulated only in tissues or at times where the sRNA molecule is expressed.

The foregoing and other features will become more apparent from the following detailed description of several embodiments, which proceeds with reference to the accompanying figures.

SEQUENCE LISTING

Figure 1:
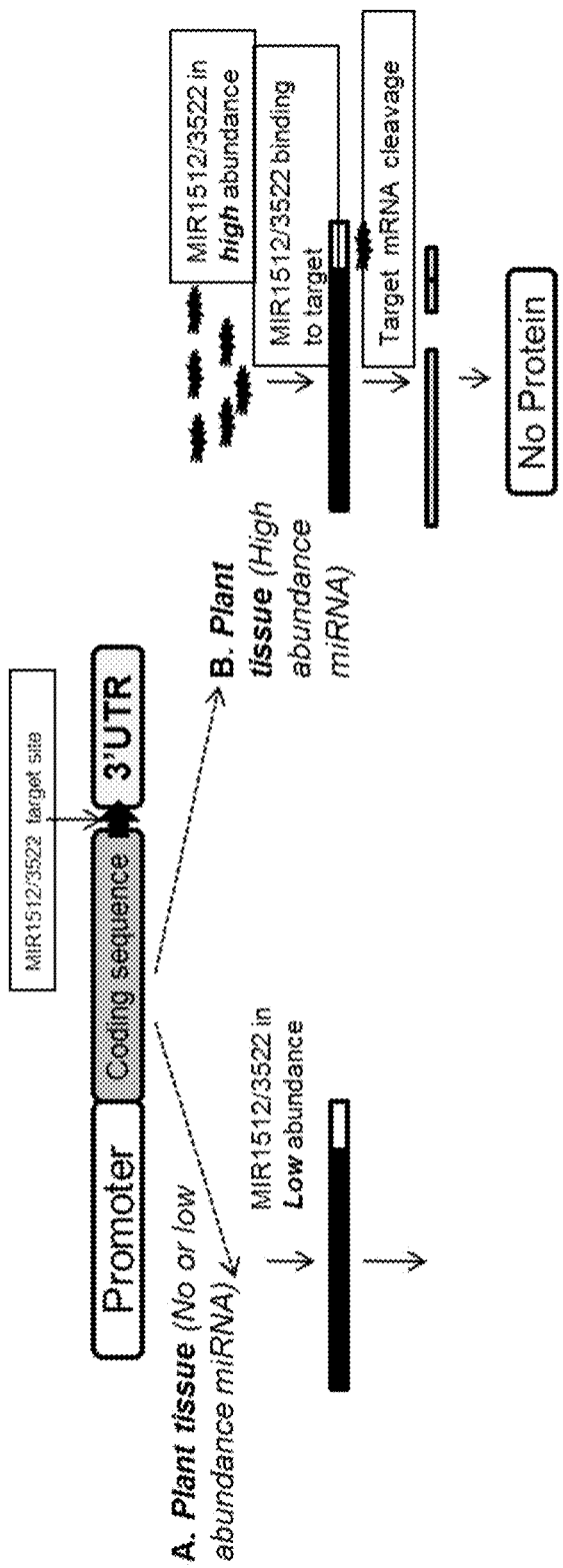
FIG. 1 is a diagram of particular embodiments, wherein tissue-specific transgene expression modulation is conferred using a target site of naturally occurring sRNA in a specific tissue.
Figure 2:
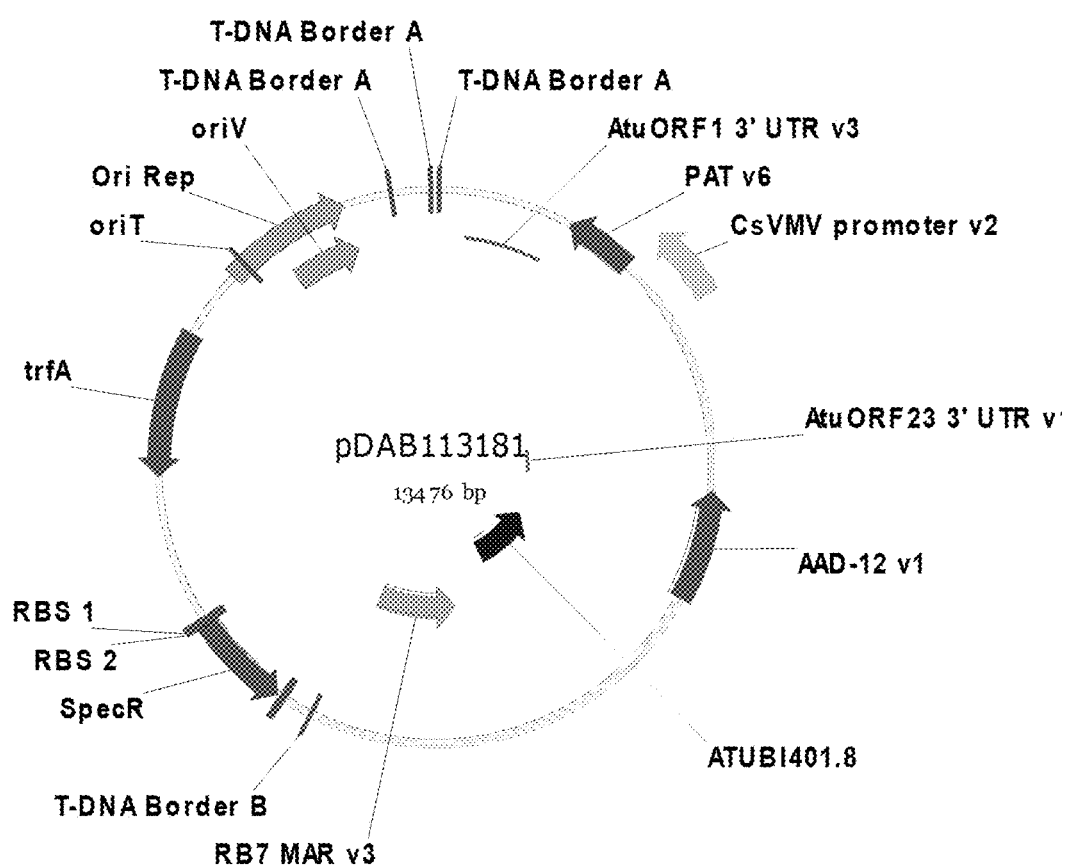
FIG. 2 is a schematic of pDAB113181 which contains AAD-12 expression cassette comprising the ATUBI401.8 promoter, AAD-12 v1 coding sequence, and the AtuORF23 3' UTR v1. Further contained on this plasmid is the pat gene expression cassette, which comprises the CsVMV promoter v2, pat v6 coding sequence, and AtuORF1 3' UTR v3 within T-DNA.
Figure 3:
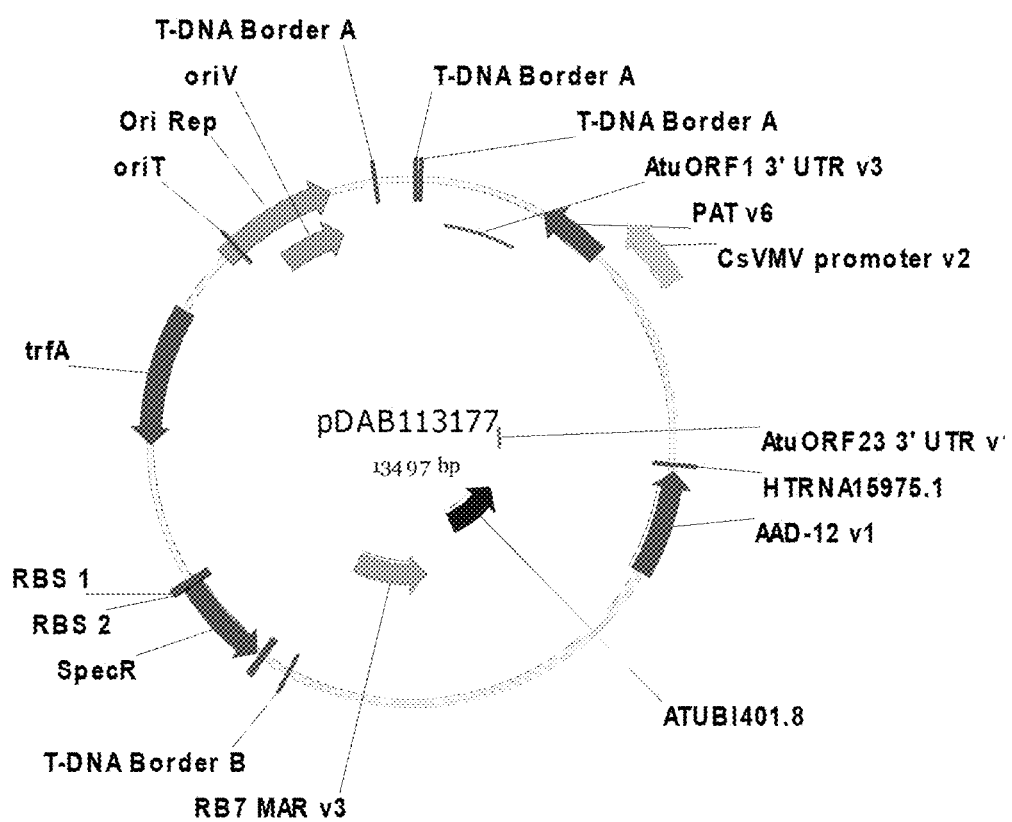
FIG. 3 is a schematic of pDAB113177 which contains AAD-12 expression cassette comprising the ATUBI401.8 promoter, AAD-12 v1 coding sequence, miR3522 target site, and the AtuORF23 3' UTR v1. Further contained on this plasmid is the pat gene expression cassette, which comprises the CsVMV promoter v2, pat v6 coding sequence, and AtuORF1 3' UTR v3 within T-DNA.
Figure 4:
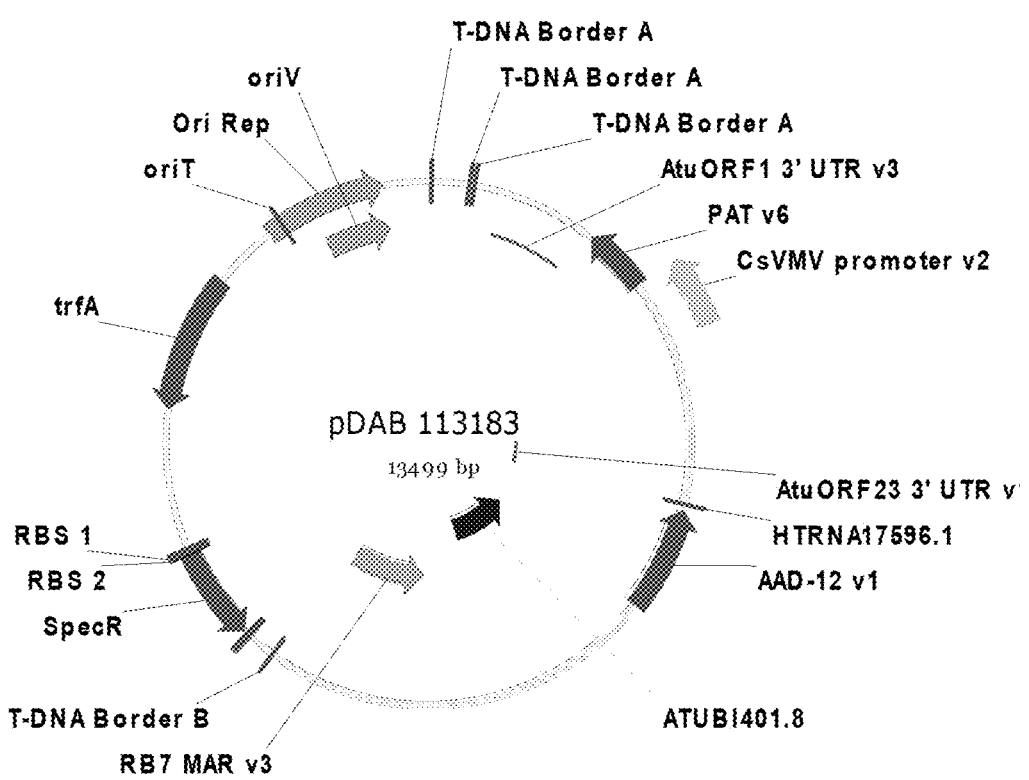
FIG. 4 is a schematic of pDAB113183 which contains AAD-12 expression cassette comprising the ATUBI401.8 promoter, AAD-12 v1 coding sequence, miR1512 target site, and the AtuORF23 3' UTR v1. Further contained on this plasmid is the pat gene expression cassette, which comprises the CsVMV promoter v2, pat v6 coding sequence, and AtuORF1 3' UTR v3 within T-DNA.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NO: 1 shows, in the 5' to 3' direction, an exemplary miR3522 RNA:

UGAGACCAAAUGAGCAGCUGA

SEQ ID NO:2 shows, in the 5' to 3' direction, an exemplary miRNA target site HTRNA15975.1 for miRNA3522 (SEQ ID NO:1):

TCAGCTGCTCATTTGGTCTCA

SEQ ID NO:3 shows, in the 5' to 3' direction, an exemplary miR1512 RNA:

UAACUGAACAUUCUUAGAGCAU

SEQ ID NO:4 in the 5' to 3' direction, an exemplary miRNA target site HTRNA15976.1 for miRNA1512 (SEQ ID NO:3):

ATGCTCTAAGAATGTTCAGTTA

SEQ ID NO:5 shows an exemplary expression cassette comprising an aad12 v1 coding region (underlined), followed by AtuORF23 3' UTR v3 (italics small case). The uppercase no underline sequence is a sequence for multiple cloning sites:

<u>ATGGCTCAGACCACTCTCCAAATCACACCCACTGGTGCCACCTTGGGT</u>

<u>GCCACAGTCACTGGTGTTCACCTTGCCACACTTGACGATGCTGGTTTC</u>

<u>GCTGCCCTCCATGCAGCCTGGCTTCAACATGCACTCTTGATCTTCCCT</u>

-continued

GGGCAACACCTCAGCAATGACCAACAGATTACCTTTGCTAAACGCTTT

GGAGCAATTGAGAGGATTGGCGGAGGTGACATTGTTGCCATATCCAAT

GTCAAGGCAGATGGCACAGTGCGCCAGCACTCTCCTGCTGAGTGGGAT

GACATGATGAAGGTCATTGTGGGCAACATGGCCTGGCACGCCGACTCA

ACCTACATGCCAGTCATGGCTCAAGGAGCTGTGTTCAGCGCAGAAGTT

GTCCCAGCAGTTGGGGGCAGAACCTGCTTTGCTGACATGAGGGCAGCC

TACGATGCCCTTGATGAGGCAACCCGTGCTCTTGTTCACCAAAGGTCT

GCTCGTCACTCCCTTGTGTATTCTCAGAGCAAGTTGGGACATGTCCAA

CAGGCCGGGTCAGCCTACATAGGTTATGGCATGGACACCACTGCAACT

CCTCTCAGACCATTGGTCAAGGTGCATCCTGAGACTGGAAGGCCCAGC

CTCTTGATCGGCCGCCATGCCCATGCCATCCCTGGCATGGATGCAGCT

GAATCAGAGCGCTTCCTTGAAGGACTTGTTGACTGGGCCTGCCAGGCT

CCCAGAGTCCATGCTCACCAATGGGCTGCTGGAGATGTGGTTGTGTGG

GACAACCGCTGTTTGCTCCACCGTGCTGAGCCCTGGGATTTCAAGTTG

CCACGTGTGATGTGGCACTCCAGACTCGCTGGACGCCCAGAAACTGAG

GGTGCTGCCTTGGTTTGAGTAGTTAGCTTAATCACCTAGAGCTCGGTC

ACCAGCATAATTTTTATTAATGTACTAAATTACTGTTTTGTTAAATGC

AATTTTGCTTTCTCGGGATTTTAA*tatcaaaatctatttagaaataca*

*caatattttgttgcaggcttgctggagaatcgatctgctatcataaaa*

*attacaaaaaaattttatttgcctcaattattttaggattggtattaa*

*ggacgcttaaattatttgtcgggtcactacgcatcattgtgattgaga*

*agatcagcgatacgaaatattcgtagtactatcgataatttatttgaa*

*aattcataagaaaagcaaacgttacatgaattgatgaaacaatacaaa*

*gacagataaagccacgcacatttaggatattggccgagattactgaat*

*attgagtaagatcacggaatttctgacaggagcatgtcttcaattcag*

*cccaaatggcagttgaaatactcaaaccgcccatatgcaggagcgga*

*tcattcattgtttgtttggttgcctttgccaacatgggagtccaaggtt*

SEQ ID NO:6 shows an exemplary expression cassette comprising an aad12 v1 coding region (underlined), followed by miRNA target site HTRNA15975.1 (bold) for miRNA3522 (SEQ ID NO: 1) and AtuORF23 3' UTR v3 (italics small case). The uppercase no underline sequence is a sequence for multiple cloning sites:

ATGGCTCAGACCACTCTCCAAATCACACCCACTGGTGCCACCTTGGGT

GCCACAGTCACTGGTGTTCACCTTGCCACACTTGACGATGCTGGTTTC

GCTGCCCTCCATGCAGCCTGGCTTCAACATGCACTCTTGATCTTCCCT

GGGCAACACCTCAGCAATGACCAACAGATTACCTTTGCTAAACGCTTT

GGAGCAATTGAGAGGATTGGCGGAGGTGACATTGTTGCCATATCCAAT

GTCAAGGCAGATGGCACAGTGCGCCAGCACTCTCCTGCTGAGTGGGAT

GACATGATGAAGGTCATTGTGGGCAACATGGCCTGGCACGCCGACTCA

ACCTACATGCCAGTCATGGCTCAAGGAGCTGTGTTCAGCGCAGAAGTT

GTCCCAGCAGTTGGGGGCAGAACCTGCTTTGCTGACATGAGGGCAGCC

TACGATGCCCTTGATGAGGCAACCCGTGCTCTTGTTCACCAAAGGTCT

GCTCGTCACTCCCTTGTGTATTCTCAGAGCAAGTTGGGACATGTCCAA

CAGGCCGGGTCAGCCTACATAGGTTATGGCATGGACACCACTGCAACT

CCTCTCAGACCATTGGTCAAGGTGCATCCTGAGACTGGAAGGCCCAGC

CTCTTGATCGGCCGCCATGCCCATGCCATCCCTGGCATGGATGCAGCT

GAATCAGAGCGCTTCCTTGAAGGACTTGTTGACTGGGCCTGCCAGGCT

CCCAGAGTCCATGCTCACCAATGGGCTGCTGGAGATGTGGTTGTGTGG

GACAACCGCTGTTTGCTCCACCGTGCTGAGCCCTGGGATTTCAAGTTG

CCACGTGTGATGTGGCACTCCAGACTCGCTGGACGCCCAGAAACTGAG

GGTGCTGCCTTGGTTTGAGTAGTTAGCTTAATCACCTAGAGCTCGGTC

AGCTGCTCATTTGGTCTCATCACCAGCATAATTTTTATTAATGTACTA

AATTACTGTTTTGTTAAATGCAATTTTGCTTTCTCGGGATTTTAA*tat*

*caaaatctatttagaaatacacaatattttgttgcaggcttgctggag*

*aatcgatctgctatcataaaaattacaaaaaaattttatttgcctcaa*

*ttattttaggattggtattaaggacgcttaaattatttgtcgggtcac*

*tacgcatcattgtgattgagaagatcagcgatacgaaatattcgtagt*

*actatcgataatttatttgaaaattcataagaaaagcaaacgttacat*

*gaattgatgaaacaatacaaagacagataaagccacgcacatttagga*

*tattggccgagattactgaatattgagtaagatcacggaatttctgac*

*aggagcatgtcttcaattcagcccaaatggcagttgaaatactcaaac*

*cgcccatatgcaggagcggatcattcattgtttgtttggttgccttt*

*gccaacatgggagtccaaggtt*

SEQ ID NO:7 shows an exemplary expression cassette comprising an aad12 v1 coding region (underlined), followed by miRNA target site HTRNA17596.1 (bold) for miRNA1512 (SEQ ID NO:3) and AtuORF23 3' UTR v3 (italics small case). The uppercase no underline sequence is a sequence for multiple cloning sites:

ATGGCTCAGACCACTCTCCAAATCACACCCACTGGTGCCACCTTGGGT

GCCACAGTCACTGGTGTTCACCTTGCCACACTTGACGATGCTGGTTTC

GCTGCCCTCCATGCAGCCTGGCTTCAACATGCACTCTTGATCTTCCCT

GGGCAACACCTCAGCAATGACCAACAGATTACCTTTGCTAAACGCTTT

GGAGCAATTGAGAGGATTGGCGGAGGTGACATTGTTGCCATATCCAAT

GTCAAGGCAGATGGCACAGTGCGCCAGCACTCTCCTGCTGAGTGGGAT

GACATGATGAAGGTCATTGTGGGCAACATGGCCTGGCACGCCGACTCA

ACCTACATGCCAGTCATGGCTCAAGGAGCTGTGTTCAGCGCAGAAGTT

GTCCCAGCAGTTGGGGGCAGAACCTGCTTTGCTGACATGAGGGCAGCC

TACGATGCCCTTGATGAGGCAACCCGTGCTCTTGTTCACCAAAGGTCT

GCTCGTCACTCCCTTGTGTATTCTCAGAGCAAGTTGGGACATGTCCAA

CAGGCCGGGTCAGCCTACATAGGTTATGGCATGGACACCACTGCAACT

CCTCTCAGACCATTGGTCAAGGTGCATCCTGAGACTGGAAGGCCCAGC

-continued

CTCTTGATCGGCCGCCATGCCCATGCCATCCCTGGCATGGATGCAGCT

GAATCAGAGCGCTTCCTTGAAGGACTTGTTGACTGGGCCTGCCAGGCT

CCCAGAGTCCATGCTCACCAATGGGCTGCTGGAGATGTGGTTGTGTGG

GACAACCGCTGTTTGCTCCACCGTGCTGAGCCCTGGGATTTCAAGTTG

CCACGTGTGATGTGGCACTCCAGACTCGCTGGACGCCCAGAAACTGAG

GGTGCTGCCTTGGTTTGAGTAGTTAGCTTAATCACCTAGAGCTCGGAT

GCTCTAAGAATGTTCAGTTATCACCAGCATAATTTTTATTAATGTACT

AAATTACTGTTTTGTTAAATGCAATTTTGCTTTCTCGGGATTTTAAta tcaaaatctatttagaaatacacaatattttgttgcaggcttgctgga gaatcgatctgctatcataaaaattacaaaaaaattttatttgcctca attattttaggattggtattaaggacgcttaaattatttgtcgggtca ctacgcatcattgtgattgagaagatcagcgatacgaaatattcgtag tactatcgataatttatttgaaaattcataagaaaagcaaacgttaca tgaattgatgaaacaatacaaagacagataaagccacgcacatttagg atattggccgagattactgaatattgagtaagatcacggaatttctga caggagcatgtcttcaattcagcccaaatggcagttgaaatactcaaa ccgcccatatgcaggagcggatcattcattgtttgtttggttgcctt tgccaacatgggagtccaaggtt SEQ ID NO:8 shows an ATUBI401.8 promoter, utilized in certain examples herein:

GTCGACCTGCAGGTCAACGGATCAGGATATTCTTGTTTAAGATGTTGA

ACTCTATGGAGGTTTGTATGAACTGATGATCTAGGACCGGATAAGTTC

CCTTCTTCATAGCGAACTTATTCAAAGAATGTTTTGTGTATCATTCTT

GTTACATTGTTATTAATGAAAAAATATTATTGGTCATTGGACTGAACA

CGAGTGTTAAATATGGACCAGGCCCCAAATAAGATCCATTGATATATG

AATTAAATAACAAGAATAAATCGAGTCACCAAACCACTTGCCTTTTTT

AACGAGACTTGTTCACCAACTTGATACAAAAGTCATTATCCTATGCAA

ATCAATAATCATACAAAAATATCCAATAACACTAAAAAATTAAAGAA

ATGGATAATTTCACAATATGTTATACGATAAAGAAGTTACTTTTCCAA

GAAATTCACTGATTTTATAAGCCCACTTGCATTAGATAAATGGCAAAA

AAAAACAAAAGGAAAAGAAATAAAGCACGAAGAATTCTAGAAAATAC

GAAATACGCTTCAATGCAGTGGGACCCACGGTTCAATTATTGCCAATT

TTCAGCTCCACCGTATATTTAAAAAATAAAACGATAATGCTAAAAAAA

TATAAATCGTAACGATCGTTAAATCTCAACGGCTGGATCTTATGACGA

CCGTTAGAAATTGTGGTTGTCGACGAGTCAGTAATAAACGGCGTCAAA

GTGGTTGCAGCCGGCACACACGAGTCGTGTTTATCAACTCAAAGCACA

AATACTTTTCCTCAACCTAAAAATAAGGCAATTAGCCAAAAACAACTT

TGCGTGTAAACAACGCTCAATACACGTGTCATTTTATTATTAGCTATT

GCTTCACCGCCTTAGCTTTCTCGTGACCTAGTCGTCCTCGTCTTTTCT

TCTTCTTCTTCTATAAAACAATACCCAAAGCTTCTTCTTCACAATTCA

GATTTCAATTTCTCAAAATCTTAAAAACTTTCTCTCAATTCTCTCTAC

CGTGATCAAGGTAAATTTCTGTGTTCCTTATTCTCTCAAAATCTTCGA

TTTTGTTTTCGTTCGATCCCAATTTCGTATATGTTCTTTGGTTTAGAT

TCTGTTAATCTTAGATCGAAGACGATTTTCTGGGTTTGATCGTTAGAT

ATCATCTTAATTCTCGATTAGGGTTTCATAAATATCATCCGATTTGTT

CAAATAATTTGAGTTTTGTCGAATAATTACTCTTCGATTTGTGATTTC

TATCTAGATCTGGTGTTAGTTTCTAGTTTGTGCGATCGAATTTGTCGA

TTAATCTGAGTTTTTCTGATTAACAG

SEQ ID NO:9 AAD12 forward nucleotide primer:

AACCCGTGCTCTTGTTC

SEQ ID NO: 10 AAD12 reverse nucleotide primer:

GGATGCACCTTGACCAAT

SEQ ID NO:11 AAD12 fluorescent probe used for transgene copy number and relative expression detection:

CAGGCCGGGTCAGCCT

SEQ ID NO: 12 PAT forward nucleotide primer:

ACAAGAGTGGATTGATGATCTAGAGAGGT

SEQ ID NO: 13 PAT reverse nucleotide primer:

CTTTGATGCCTATGTGACACGTAAACAGT

SEQ ID NO: 14 PAT fluorescent probe used for transgene copy number and relative expression detection:

GGTGTTGTGGCTGGTATTGCTTACGCTGG

SEQ ID NO: 15 Spec forward nucleotide primer:

CGCCGAAGTATCGACTCAACT

SEQ ID NO: 16 Spec reverse nucleotide primer:

GCAACGTCGGTTCGAGATG

SEQ ID NO: 17 Spec fluorescent probe used for transgene copy number and relative expression detection:

TCAGAGGTAGTTGGCGTCATCGAG

SEQ ID NO: 18 GMS116 forward nucleotide primer:

GTAATATGGGCTCAGAGGAATGGT

SEQ ID NO: 19 GMS116 reverse nucleotide primer:

ATGGAGAAGAACATTGGAATTGC

SEQ ID NO:20 GMS116 fluorescent probe used for transgene copy number and relative expression detection:

CCATGGCCCGGTACCATCTGGTC

SEQ ID NO:21 Soy Actin forward nucleotide primer:

GTGACTCACACCATCACCAGAGT

SEQ ID NO:22 Soy Actin reverse nucleotide primer:

ATCCAGGCTGTCCTCTCCCTATA

SEQ ID NO:23 Soy Actin fluorescent probe used for transgene copy number and relative expression detection:

CAATACCAGTTGTGCGACC

DETAILED DESCRIPTION

I. Overview of Several Embodiments

Embodiments herein exploit tissue-specific expression of sRNAs to repress/knockdown the expression of a transgene in the specific tissue. sRNAs have been shown to regulate diverse developmental processes, including organ separation, polarity, and identity, and to modulate their own biogenesis and function. In embodiments herein, the precision and specificity of sRNA-mediated gene regulation is utilized to accomplish the tissue-specific expression of a transgene. In examples, a target site for a tissue-specific sRNA (e.g., an endogenous tissue-specific sRNA, including a miRNA or a siRNA) is engineered into the transgene to reduce or eliminate expression of the transgene in the tissue. Embodiments herein may be utilized to target the expression of any transgene to any particular tissue(s).

Particular embodiments herein are useful, for example, in preferentially repressing expression of transgenes in specific tissues, cell types or developmental stages while continuing to obtain high expression in other tissues, cells or developmental stages. The method provides unique means of transgene expression modulation that overcome limitations of conventional transgene expression regulated by promoters. Examples include repression of certain transgene(s): interfering during transformation and tissue culture stages for transgenic plant production; pollen, egg cell, zygote or other reproductive stage for seed production; root tissue for plant health; seed tissue when the transgene trait is not required in seed; diversified transgene expression modulation when multiple transgenes are regulated by one promoter.

II. Abbreviations

RNA ribonucleic acid
dsRNA double-stranded ribonucleic acid
DCL DICER-LIKE proteins
ELISAs Enzyme Linked Immunosorbant Assays
RDRs RNA-Dependent RNA Polymerases
GI growth inhibition
NCBI National Center for Biological Information
gDNA genomic DNA
iRNA inhibitory ribonucleic acid
ORF open reading frame
RNAi ribonucleic acid interference
miRNA micro inhibitory ribonucleic acid
sRNA small ribonucleic acid
siRNA small inhibitory ribonucleic acid, or short, interfering ribonucleic acid
hpRNA hairpin ribonucleic acid
RT room temperature
BSA bovine serum albumin
UTR untranslated region
PCR polymerase chain reaction
RISC RNA-induced Silencing Complex III. Terms In the description and tables which follow, a number of terms are used. In order to provide a clear and consistent understanding of the specification and claims, including the scope to be given such terms, the following definitions are provided:

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Expression: As used herein, "expression" of a nucleic acid sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein, but also including production of an sRNA. Gene expression can be influenced by external signals; for example, exposure of a cell, tissue, or organism to an agent that increases or decreases gene expression. Expression of a gene can also be regulated anywhere in the pathway from DNA to RNA to protein. Expression of a gene can also be regulated "predominantly" in a specific cell, tissue or organ, or at a particular time (e.g., during development or differentiation). Expression of a gene is "predominant" when there is approximately <60% expression in other non-specific cell, tissue or organ, or stage. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Genetic material: As used herein, the term "genetic material" includes all genes, and nucleic acid molecules, such as DNA and RNA.

Inhibition/downregulation: As used herein, the terms "inhibition" and "downregulation," when used to describe an effect on a coding sequence (for example, a gene), are used interchangeably and refer to a measurable decrease in the cellular level of mRNA transcribed from the coding sequence and/or peptide, polypeptide, or protein product of the coding sequence. In some examples, expression of a coding sequence may be inhibited such that expression is essentially eliminated (e.g., expression is reduced to less than 10%, 9%, 8%, 7%, 6%, 5%, 4%, 3%, 2%, or 1% of its expression in a control cell).

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods, wherein there has been a chemical or functional change in the nucleic acid or protein. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include single strands or both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The nucleotide sequence of a nucleic acid molecule is read from the 5' to the 3' end of the molecule by convention. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double-stranded RNA), sRNA (small RNA), siRNA (small interfering RNA), miRNA (micro-RNA), hpRNA (hairpin RNA), mRNA (messenger RNA), tRNA (transfer RNA), and cRNA (complementary RNA). The term "deoxyribonucleic acid" (DNA) is inclusive of cDNA, genomic DNA, and DNA-RNA hybrids. The term "polynucleotide" will be understood by those in the art as a structural term that is defined by its nucleotide sequence, and that includes genomic sequences, ribosomal RNA sequences, transfer RNA sequences, messenger RNA sequences, operon sequences, and smaller engineered nucleotide sequences.

Small RNA (sRNA): sRNAs are non-coding RNAs that regulate gene expression by pairing to the message of protein-coding genes to guide mRNA cleavage or repression of productive translation. Dugas and Bartel (2004) Curr. Opin. Plant Biolo. 7: 512-20. As used herein, the term "small RNA" (sRNA) includes, for example, microRNA (miRNA), small interfering RNA (siRNA), trans-acting small interfering RNA (tasiRNA), and other sRNAs guiding cleavage, translational repression, and/or gene silencing.

Small interfering RNA (siRNA): RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then is associated with a multi-subunit complex, the RNAi-induced silencing complex (RISC). A typical function of the siRNA is to guide RISC to the target based on base-pair complementarity.

Target nucleic acid (to be inhibited): As used herein, the term "target" or "target site" in reference to a polynucleotide, refers to any nucleic acid containing a sequence that interacts with a miRNA or siRNA, or that has the potential to yield a sequence that interacts with a miRNA or siRNA (for example, through transcription of a locus). The target can be a cellular nucleic acid, such as an mRNA that encodes an essential or nonessential protein, or a foreign nucleic acid, such as a transgene-derived RNA molecule comprising a gene of interest linked to a target site for a specific sRNA. The target can be a DNA sequence corresponding to a promoter, or a sequence corresponding to any expressed region of a genome, for instance.

Oligonucleotide: An oligonucleotide is a short nucleic acid molecule. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence" refers to a nucleotide sequence that is transcribed into RNA when placed under the control of appropriate regulatory sequences. A "protein coding sequence" is a nucleotide sequence (DNA or RNA) that is ultimately translated into a polypeptide, via transcription and mRNA. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell.

Endogenous: The term "endogenous," as applied to nucleic acids (e.g., polynucleotides, DNA, RNA (including sRNA), and genes) herein, refers to one or more nucleic acid(s) that are normally (e.g., in a wild-type cell of the same type and species) present within their specific environment or context. For example, an endogenous gene is one that is normally found in the particular cell in question and in the same context (e.g., with regard to regulatory sequences). Endogenous nucleic acids can be distinguished from exogenous and/or heterologous, for example and without limitation, by detection in the latter of sequences that are consequent with recombination from bacterial plasmid; identification of atypical codon preferences; and amplification of atypical sequences in a PCR reaction from primers characterized in a wild-type cell.

Exogenous: The term "exogenous," as applied to nucleic acids herein, refers to one or more nucleic acid(s) that are not normally present within their specific environment or context. For example, if a host cell is transformed with a nucleic acid that does not occur in the untransformed host cell in nature, then that nucleic acid is exogenous to the host cell. The term exogenous, as used herein, also refers to one or more nucleic acid(s) that are identical in sequence to a nucleic acid already present in a host cell, but that are located in a different cellular or genomic context than the nucleic acid with the same sequence already present in the host cell. For example, a nucleic acid that is integrated in the genome of the host cell in a different location than a nucleic acid with the same sequence is normally integrated in the genome of the host cell is exogenous to the host cell. Furthermore, a nucleic acid (e.g., a DNA molecule) that is present in a plasmid or vector in the host cell is exogenous to the host cell when a nucleic acid with the same sequence is only normally present in the genome of the host cell.

Heterologous: The term "heterologous," as applied to nucleic acids (e.g., polynucleotides, DNA, RNA, and genes) herein, means of different origin. For example, if a host cell is transformed with a nucleic acid that does not occur in the untransformed host cell in nature, then that nucleic acid is heterologous (and exogenous) to the host cell. Furthermore, different elements (e.g., promoter, enhancer, coding sequence, terminator, etc) of a transforming nucleic acid may be heterologous to one another and/or to the transformed host. The term heterologous, as used herein, may also be applied to one or more nucleic acid(s) that are identical in sequence to a nucleic acid already present in a host cell, but that are now linked to different additional sequences and/or are present at a different copy number, etc.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2: 482; Needleman and Wunsch (1970) J. Mol. Biol. 48: 443; Pearson and Lipman (1988) Proc. Natl. Acad. Sci. U.S.A. 85: 2444; Higgins and Sharp (1988) Gene 73: 237-44; Higgins and Sharp (1989) CABIOS 5: 151-3; Corpet et al. (1988) Nucleic Acids Res. 16: 10881-90; Huang et al. (1992) Comp. Appl. Biosci. 8: 155-65; Pearson et al. (1994) Methods Mol. Biol. 24: 307-31; Tatiana et al. (1999) FEMS Microbiol. Lett. 174: 247-50. A detailed consideration of sequence alignment methods and homology calculations can be found in, e.g., Altschul et al. (1990) J. Mol. Biol. 215: 403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

Specifically hybridizable/specifically complementary: As used herein, the terms "specifically hybridizable" and "specifically complementary" are terms that indicate a sufficient degree of complementarity such that stable and specific binding occurs between the nucleic acid molecule and a target nucleic acid molecule. Hybridization between two nucleic acid molecules involves the formation of an antiparallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a polynucleotide, refers to polynucleotides that hybridize under stringent conditions to the reference nucleic acid sequence. For example, polynucleotides that are substantially homologous to a reference DNA coding sequence are those polynucleotides that hybridize under stringent conditions (e.g., the Moderate Stringency conditions set forth, supra) to the reference DNA coding sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

DNA has two antiparallel strands, a 5'->>3' strand, referred to as the plus strand, and a 3'->>5' strand, referred to as the minus strand. Because RNA polymerase adds nucleic acids in a 5'->>3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA is a molecule of RNA complementary to a sense (encoding) nucleic acid molecule.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, the term "substantially identical" may refer to nucleotide sequences that are more than 85% identical. For example, a substantially identical nucleotide sequence may be at least 85.5%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell.

Some embodiments herein include a "plant promoter." A plant promoter is a promoter that is capable of initiating transcription in a plant cell.

Some embodiments herein include a "tissue-preferred promoter." A tissue-preferred promoter is a promoter that is capable of initiating transcription under developmental control, and include, for example and without limitation: promoters that preferentially initiate transcription in leaves, pollen, tassels, roots, seeds, fibers, xylem vessels, tracheids, and sclerenchyma. Promoters that initiate transcription essentially only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters.

Any inducible promoter may be used in some embodiments of the invention. See Ward et al. (1993) Plant Mol. Biol. 22: 361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88: 10421-5).

In contrast to non-constitutive promoters, a "constitutive" promoter is a promoter that is active under most environmental conditions. Exemplary constitutive promoters include, but are not limited to: promoters from plant viruses, such as the 35S promoter from CaMV; promoters from rice actin genes; ubiquitin promoters; pEMU; MAS; maize H3 histone promoter; and the ALS promoter, Xba1/Nco1 fragment 5' to the *Brassica napus* ALS3 structural gene (or a nucleotide sequence similarity to said Xba1/Nco1 fragment) (PCT International Patent Publication No. WO 96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: a root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Trait or phenotype: The terms "trait" and "phenotype" are used interchangeably herein. For the purposes of the present disclosure, traits of particular interest include agronomically important traits, as may be expressed, for example, in a crop plant. In some examples, a trait of particular interest is herbicide tolerance.

Transformation: As used herein, the term "transformation" refers to the transfer of one or more nucleic acid molecule(s) into a cell. A cell is "transformed" by a nucleic acid molecule introduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319: 791-3); lipofection (Felgner et al. (1987) Proc. Natl. Acad. Sci. USA 84: 7413-7); microinjection (Mueller et al. (1978) Cell 15: 579-85); *Agrobacterium*-mediated transfer (Fraley et al. (1983) Proc. Natl. Acad. Sci. USA 80: 4803-7); direct DNA uptake; and microprojectile bombardment (Klein et al. (1987) Nature 327: 70).

Transgene: A transgene is an exogenous nucleic acid sequence. In some examples, a transgene may be a sequence that encodes one or both strand(s) of a dsRNA molecule that comprises a nucleotide sequence that is complementary to a target nucleic acid. In some examples, a transgene may be an antisense nucleic acid sequence, the expression of which inhibits expression of a target nucleic acid. In still other examples, a transgene may be a gene sequence (e.g., a herbicide-tolerance gene), a gene encoding an industrially or pharmaceutically useful compound, or a gene encoding a desirable agricultural trait. In these and other examples, a transgene may contain regulatory sequences operably linked to the coding sequence of the transgene (e.g., a promoter).

Vector: A vector refers to a nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; and a virus that carries exogenous DNA into a cell. A vector may also include one or more expression cassettes comprising genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Unless specifically indicated or implied, the terms "a", "an", and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology*

*and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acids and Systems

Plants and animals use sRNAs to direct the post-transcriptional and epigenetic regulation of target genes. Many miRNAs and their corresponding target sequences are highly conserved. For example, target sequences in plants that are recognized by related miRNAs in different species often differ only by several nucleotides. Therefore, the computational prediction of target sites is possible. Jones-Rhoades and Bartel (2004) Mol. Cell 14: 787-99. Additionally, a functional sRNA target site from one plant species is likely to be functional in a different plant species that expresses the targeting sRNA. For example, miRNA target genes from *Arabidopsis* heterologously expressed in *Nicotiana* are cleaved by endogenous *Nicotiana* miRNAs. Llave et al. (2002) Science 297: 2053-6.

Embodiments herein include nucleic acids comprising a target site for at least one sRNA molecule. A target site for an sRNA molecule may be, for example, between about 20-30 nucleotides in length. For example, such a target site may be between about 20-25 or 20-21 nucleotides in length. In particular examples, the target site may be 19, about 20, about 21, about 22, about 23, about 24, about 25, about 26, about 27, about 28, about 29, about 30, or 31 nucleotides in length. Target sites for particular sRNAs may be identified or engineered computationally, using program parameters that may be selected within the discretion of those skilled in the art. Target sites may be identified or engineered to be specifically targeted by a single sRNA, or to be targeted by a group of related sRNAs.

Particular embodiments include nucleic acid expression cassettes, comprising, for example, a gene or coding region of interest that comprises an sRNA target site (e.g., an internal target site that is located within a transcribed portion of the gene or coding region), such that co-expression in a cell of the gene or coding region of interest and the targeting sRNA results in downregulated, including essentially eliminated, expression of the gene or coding region. Such nucleic acids may be, for example and without limitation, a heterologous or exogenous nucleic acid in the genome of a cell (e.g., a plant cell), or a vector.

In some embodiments, a nucleic acid comprising a gene or coding region of interest with an sRNA target site further comprises one or more regulatory sequences that are operably linked to the gene or coding region of interest, so as to effect the transcription of the gene or coding region of interest in a cell; i.e., an expression construct. In examples, the cell is a plant cell. In particular embodiments, the gene or coding region of interest is operably linked to a constitutive plant promoter in the expression construct. By, for example, transforming a plant cell or tissue with such an expression construct and regenerating a plant from the plant cell or tissue, a transgenic plant may be produced, wherein the gene or coding region of interest is transcribed in every cell or essentially every cell of the plant.

The nucleic acid sequence of interest may be any nucleic acid sequence that provides for, or enhances, a beneficial feature of a resultant transgenic plant. Particularly useful nucleic acid sequences are those that encode proteins or antisense RNA transcripts in order to promote increased nutritional values, higher yields, tolerance to herbicides, insects, or diseases, and the like. In embodiments, the gene or coding region of interest may be an agronomic gene or nucleotide sequence encoding a polypeptide of interest, and may also and/or alternatively include, for example and without limitation: genes that confer tolerance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) EMBO J. 7: 1241, and Miki et al. (1990) Theor. Appl. Genet. 80: 449, respectively); glyphosate tolerance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexanediones (ACCase inhibitor-encoding genes). See, e.g., U.S. Pat. Nos. 4,940,835 and 6,248,876 (nucleotide sequences of forms of EPSPs which can confer glyphosate tolerance to a plant). A DNA molecule encoding a mutant aroA gene can be obtained under ATCC accession number 39256. See also U.S. Pat. No. 4,769,061 (nucleotide sequence of a mutant aroA gene). European patent application No. 0 333 033 and U.S. Pat. No. 4,975,374 disclose nucleotide sequences of glutamine synthetase genes, which may confer tolerance to herbicides such as L-phosphinothricin. Nucleotide sequences of exemplary PAT genes are provided in European application No. 0 242 246, and DeGreef et al. (1989) Bio/Technology 7: 61 (production of transgenic plants that express chimeric bar genes coding for PAT activity). Exemplary of genes conferring tolerance to phenoxy proprionic acids and cyclohexanediones, such as sethoxydim and haloxyfop, include the Acc1-S1, Acc1-S2 and Acc1-S3 genes described by Marshall et al. (1992) Theor. Appl. Genet. 83:435. GAT genes capable of conferring glyphosate tolerance are described, for example, in WO 2005012515. Genes conferring tolerance to 2,4-D, phenoxyproprionic acid and/or pyridyloxy auxin herbicides are described, for example, in WO 2005107437 and WO 2007053482.

Nucleic acids comprising an agronomic gene or nucleotide sequence encoding a polypeptide of interest may also include, for example and without limitation: nitrogen use efficiency gene, water use efficiency gene, nutritional quality gene (e.g., modified oil profile), or a gene conferring tolerance to an herbicide that inhibits photosynthesis, such as a triazine (psbA and gs+ genes) or a benzonitrile (nitrilase gene). See, e.g., Przibila et al. (1991) Plant Cell 3: 169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

Embodiments herein also or alternatively include a set of nucleic acids, wherein the set includes at least one nucleic acid comprising a target site for at least one sRNA molecule. In some embodiments, the set of nucleic acids further includes at least one nucleic acid encoding at least one sRNA molecule targeting the nucleic acid comprising the target site therefore. In particular embodiments, a plant cell may be transformed (either in one step or in multiple steps)

with the nucleic acids of the set. In examples, when a transgenic plant tissue or plant is regenerated from the transformed plant cell, the nucleic acid comprising the target site for the at least one sRNA molecule is expressed essentially in all cells other than those wherein the sRNA molecule is expressed. Thus, when the set of nucleic acids includes a nucleic acid encoding the sRNA molecule under the control of a tissue-specific promoter, the nucleic acid comprising the target site for the at least one sRNA molecule is expressed essentially in all cells other than cells of the tissue wherein the promoter directs expression of the sRNA molecule.

In embodiments, the gene or coding region of interest may be genes that confer resistance to insect pests, such as Cry1A, Cry1C, Cry1D, Cry1E, Cry1F, Cry2A, VIP3, and Cry9. In some embodiments, the nucleic acid sequences will be useful genes which are inherently unstable due to their relatively large size (at least 4-5 kb in length), which is known to render the genes more susceptible to physical, chemical, or enzymatic degradation. Genes inherently unstable due to their size include insecticidal genes from *Xenorhabdus* (see U.S. Pat. No. 6,048,838) and *Photorabdus* (e.g., Toxin A).

In one embodiment, one or more nucleic acids contain one or more sRNA target sites of the present invention which have been "stacked" in relation to one another in a particular plant. By use of the phrase "stacked" or "stacking", it is meant herein that multiple genes of interest, each gene of interest preferably conferring a commercially desirable trait, have been transgenically introduced into a single plant. For example, a corn hybrid with stacked genes might contain genes for the insect resistance (e.g., Cry1F B.t. genes) as well as herbicide resistance genes (e.g., glyphosate resistance genes).

In some embodiments, one or more sRNA target site sequence(s) of the present invention are functionally linked to a Toxin A gene from *Photorabdus*, which is then stacked with one or more insecticide and/or herbicide resistance genes in a single crop variety. In some embodiments, the insecticide gene(s) will be from a *Bacillus thuringiensis* or *Xenorhabdus* spp., and the herbicide gene(s) will be one or more of a glufosinate, glyphosate, imidazolinone, 2,4-D or sulfonyl urea resistance gene. Of course, any of the "stacked" insecticide or herbicide genes may be functionally linked to the miRNA target site of the present invention.

The nucleic acid sequence of interest may be derived in whole or in part from a bacterial genome or episome, eukaryotic genomic, mitochondrial or plastid DNA, cDNA, viral nucleic acid, or chemically synthesized nucleic acid. It is contemplated that the nucleic acid sequence of interest may contain one or more modifications in either the coding region which could affect the biological activity or the chemical structure of the expression product, the rate of expression, or the manner of expression control. Such modifications include, but are not limited to, mutations, insertions, deletions, rearrangements and substitutions of one or more nucleotides. The nucleic acid sequence of interest may constitute an uninterrupted coding sequence or it may include one or more introns, bounded by the appropriate plant-functional splice junctions. The nucleic acid sequence of interest may be a composite of segments derived from a plurality of sources, naturally occurring or synthetic. The structural nucleic acid sequence of interest may also encode a fusion protein, so long as the experimental manipulations maintain functionality in the joining of the coding sequences.

In a further embodiment, one or more miRNA target site sequence(s) are operably linked to a transgene, wherein the transgene can be an insecticidal resistance transgene (e.g., B.t. or dsRNA), an herbicide tolerance transgene, a nitrogen use efficiency transgene, a water use efficiency transgene, a nutritional quality transgene, a DNA binding transgene, a selectable marker transgene, or combinations thereof.

V. Methods

In some embodiments herein, a plant cell, plant part, and/or plant may be genetically modified to comprise at least one nucleic acid comprising a target site for at least one sRNA molecule by any of several methods of introducing a heterologous molecule known in the art, thereby producing a non-natural transgenic plant cell, plant part, or plant. In particular embodiments herein, a heterologous molecule is introduced into a plant cell, plant part, and/or plant by a method selected from, for example and without limitation: transformation and selective breeding (e.g., backcross breeding).

In some embodiments, the nucleic acid is selected such that the target site is a target of an endogenous sRNA of the plant wherein the heterologous nucleic acid is introduced. In particular embodiments, the target site is the target site of an endogenous sRNA of the plant that is endogenously expressed in the plant in a tissue-specific, tissue-preferred, or cell type-specific manner. "Tissue-preferred" sRNA expression means preferential expression in certain tissues, and include, for example and without limitation: sRNA that are preferentially expressed in leaves, pollen, tassels, roots, seeds, fibers, xylem vessels, tracheids, and sclerenchyma. sRNA expression essentially only in certain tissues is referred to as "tissue-specific." A "cell type-specific" sRNA is primarily expressed in certain cell types in one or more organs, for example, vascular cells in roots or leaves.

Depending on the particular target gene and the level of production of the sRNA, embodiments herein may provide partial or complete downregulation of expression, or function, of the target gene. The inhibition in target gene of interest expression in different embodiments is at least a 5%, at least a 10%, at least a 20%, at least a 30%, at least a 50%, at least a 75%, at least an 80%, at least an 85%, at least a 90%, at least a 95%, or a 100% inhibition in target gene of interest expression. Any plant species or plant cell may be genetically modified to comprise a heterologous nucleic acid herein. In some embodiments, the plant cell that is so genetically modified is capable of regeneration to produce a plant. In some embodiments, plant cells that are genetically modified (e.g., host plant cells) include cells from, for example and without limitation, a higher plant, a dicotyledonous plant, a monocotyledonous plants, a consumable plant, a crop plant, and a plant utilized for its oils (e.g., an oilseed plant). Such plants include, for example and without limitation: alfalfa; soybean; cotton; rapeseed (canola); linseed; corn; rice; *Brachiaria*; wheat; safflower; sorghum; sugarbeet; sunflower; tobacco; and grasses (e.g., turf grass). In particular examples, a genetically modified plant cell or plant herein includes, for example and without limitation: rapeseed (*Brassica napus*); Indian mustard (*Brassica juncea*); Ethiopian mustard (*Brassica carinata*); turnip (*Brassica rapa*); cabbage (*Brassica oleracea*); soybean (*Glycine max*); *Linum usitatissimum*; corn (*Zea mays*); *Carthamus tinctorius; Helianthus annuus*; tobacco (*Nicotiana tabacum*); *Arabidopsis thaliana*, Brazil nut (*Betholettia excelsa*); castor bean (*Ricinus communis*); coconut (*Cocus nucifera*); coriander (*Coriandrum sativum*); cotton (*Gossypium* spp.);

groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); *Triticum* spp. (including *Triticum durum* and *Triticum aestivum*); and duckweed (*Lemnaceae* sp.). In some embodiments, the plant may have a particular genetic background, as for elite cultivars, wild-type cultivars, and commercially distinguishable varieties.

According to methods known in the art, nucleic acids can be introduced into essentially any plant. Embodiments herein may employ any of the many methods for the transformation of plants (and production of genetically modified plants) that are known in the art. Such methods include, for example and without limitation, biological and physical transformation protocols for dicotyledenous plants, as well as monocotyledenous plants. See, e.g., Goto-Fumiyuki et al. (1999) Nat. Biotechnol. 17:282-6; Miki et al. (1993) *Methods in Plant Molecular Biology and Biotechnology* (Glick, B. R. and Thompson, J. E., Eds.), CRC Press, Inc., Boca Raton, Fla., pp. 67-88. In addition, vectors and in vitro culture methods for plant cell and tissue transformation and regeneration of plants are described, for example, in Gruber and Crosby (1993) *Methods in Plant Molecular Biology and Biotechnology*, supra, at pp. 89-119.

Plant transformation techniques available for introducing a nucleic acid into a plant host cell include, for example and without limitation: transformation with disarmed T-DNA using *Agrobacterium tumefaciens* or *A. rhizogenes* as the transformation agent; calcium phosphate transfection; polybrene transformation; protoplast fusion; electroporation (D'Halluin et al. (1992) Plant Cell 4:1495-505); ultrasonic methods (e.g., sonoporation); liposome transformation; microinjection; contact with naked DNA; contact with plasmid vectors; contact with viral vectors; biolistics (e.g., DNA particle bombardment (see, e.g., Klein et al. (1987) Nature 327:70-3) and microparticle bombardment (Sanford et al. (1987) Part. Sci. Technol. 5:27; Sanford (1988) Trends Biotech. 6:299, Sanford (1990) Physiol. Plant 79:206; and Klein et al. (1992) Biotechnology 10:268); silicon carbide WHISKERS-mediated transformation (Kaeppler et al. (1990) Plant Cell Rep. 9:415-8); nanoparticle transformation (see, e.g., U.S. Patent Publication No. US2009/0104700A1); aerosol beaming; and polyethylene glycol (PEG)-mediated uptake. In specific examples, a heterologous nucleic acid may be introduced directly into the genomic DNA of a plant cell.

A widely utilized method for introducing an expression vector into a plant is based on the natural transformation system of *Agrobacterium*. Horsch et al. (1985) Science 227:1229. *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado (1991) Crit. Rev. Plant. Sci. 10:1. Details regarding *Agrobacterium* vector systems and methods for *Agrobacterium*-mediated gene transfer are also available in, for example, Gruber et al., supra, Miki et al., supra, Moloney et al. (1989) Plant Cell Reports 8:238, and U.S. Pat. Nos. 4,940,838 and 5,464,763.

If *Agrobacterium* is used for the transformation, the DNA to be inserted typically is cloned into special plasmids; either into an intermediate vector or a binary vector. Intermediate vectors cannot replicate themselves in *Agrobacterium*. The intermediate vector may be transferred into *A. tumefaciens* by means of a helper plasmid (conjugation). The Japan Tobacco Superbinary system is an example of such a system (reviewed by Komari et al. (2006) *Methods in Molecular Biology* (K. Wang, ed.) No. 343; *Agrobacterium Protocols*, $2^{nd}$ Edition, Vol. 1, Humana Press Inc., Totowa, N.J., pp. 15-41). Binary vectors can replicate themselves both in *E. coli* and in *Agrobacterium*. Binary vectors comprise a selection marker gene and a linker or polylinker which are framed by the right and left T-DNA border regions. They can be transformed directly into *Agrobacterium* (Holsters, 1978). The *Agrobacterium* comprises a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) Nuc. Acid Res. 12:8711-21) or the co-cultivation procedure (Horsch et al. (1985) Science 227:1229-31). Generally, the *Agrobacterium* transformation system is used to engineer dicotyledonous plants. Bevan et al. (1982) Ann. Rev. Genet 16:357-84; Rogers et al. (1986) Methods Enzymol. 118:627-41. The *Agrobacterium* transformation system may also be used to transform, as well as transfer, nucleic acids to monocotyledonous plants and plant cells. See U.S. Pat. No. 5,591,616; Hernalsteen et al. (1984) EMBO J 3:3039-41; Hooykass-Van Slogteren et al. (1984) Nature 311:763-4; Grimsley et al. (1987) Nature 325:1677-9; Boulton et al. (1989) Plant Mol. Biol. 12:31-40; and Gould et al. (1991) Plant Physiol. 95:426-34.

The genetic manipulations of a recombinant host herein may be performed using standard genetic techniques and screening, and may be carried out in any host cell that is suitable to genetic manipulation. In some embodiments, a recombinant host cell may be any organism or microorganism host suitable for genetic modification and/or recombinant gene expression. In some embodiments, a recombinant host may be a plant. Standard recombinant DNA and molecular cloning techniques used here are well-known in the art and are described in, for example and without limitation: Sambrook et al. (1989), supra; Silhavy et al. (1984) *Experiments with Gene Fusions*, Cold Spring Harbor Laboratory Press, Cold Spring Harbor, N.Y.; and Ausubel et al. (1987) *Current Protocols in Molecular Biology*, Greene Publishing Assoc. and Wiley-Interscience, New York, N.Y.

Following the introduction of a nucleic acid into a plant cell, the plant cell may be grown, and upon emergence of differentiating tissue such as shoots and roots, mature plants can be generated. In some embodiments, a plurality of plants can be generated. Methodologies for regenerating plants are known to those of ordinary skill in the art and can be found, for example, in: *Plant Cell and Tissue Culture* (Vasil and Thorpe, Eds.), Kluwer Academic Publishers, 1994. Genetically modified plants described herein may be cultured in a fermentation medium or grown in a suitable medium such as soil. In some embodiments, a suitable growth medium for higher plants may be any growth medium for plants, including, for example and without limitation; soil, sand, any other particulate media that support root growth (e.g., vermiculite, perlite, etc.) or hydroponic culture, as well as suitable light, water and nutritional supplements that facilitate the growth of the higher plant.

Transformed plant cells which are produced by any of the above transformation techniques can be cultured to regenerate a whole plant that possesses the transformed genotype, and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al. (1983) "Protoplasts Isolation and Culture," in *Handbook of Plant Cell Culture*, Macmillian Publishing Company, New York, pp. 124-176; and Binding (1985) *Regeneration of Plants, Plant Protoplasts*, CRC Press, Boca Raton, pp. 21-73. Regeneration can also be performed from plant callus, explants, organs, pollens, embryos or parts thereof. Such regeneration techniques are described generally in Klee et al. (1987) Ann. Rev. Plant Phys. 38:467-86.

In other embodiments, the plant cells which are transformed are not capable of regeneration to produce a plant. Such cells may be employed, for example, in developing a plant cell line having a relevant phenotype, for example, herbicide tolerance and/or male sterility.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the 0-glucuronidase, luciferase, or gfp genes) that may be present on the recombinant nucleic acid constructs. Such selection and screening methodologies are well known to those skilled in the art.

A transgenic plant containing a heterologous molecule herein can be produced through selective breeding, for example, by sexually crossing a first parental plant comprising the molecule, and a second parental plant, thereby producing a plurality of first progeny plants. A first progeny plant may then be selected that is resistant to a selectable marker (e.g., glyphosate, tolerance to which may be conferred upon the progeny plant by the heterologous molecule herein). The first progeny plant may then be selfed, thereby producing a plurality of second progeny plants. Then, a second progeny plant may be selected that is tolerant to the selectable marker. These steps can further include the backcrossing of the first progeny plant or the second progeny plant to the second parental plant or a third parental plant.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A nucleic acid may also be introduced into a predetermined area of the plant genome through homologous recombination. Methods to stably integrate a polynucleotide sequence within a specific chromosomal site of a plant cell via homologous recombination have been described within the art. For instance, site specific integration as described in US Patent Application Publication No. 2009/0111188 A1 involves the use of recombinases or integrases to mediate the introduction of a donor polynucleotide sequence into a chromosomal target. In addition, PCT International Patent Publication No. WO 2008/021207 describes zinc finger mediated-homologous recombination to stably integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to stably integrate a polynucleotide sequence into a specific chromosomal site. Finally, the use of meganucleases for targeting donor polynucleotides into a specific chromosomal location is described in Puchta et al. (1996) Proc. Natl. Acad. Sci. USA 93:5055-60.

Other various methods for site specific integration within plant cells are generally known and applicable. Kumar et al. (2001) Trends Plant Sci. 6(4):155-9. Furthermore, site-specific recombination systems that have been identified in several prokaryotic and lower eukaryotic organisms may be applied for use in plants. Examples of such systems include, but are not limited to; the R/RS recombinase system from the pSR1 plasmid of the yeast *Zygosaccharomyces rouxii* (Araki et al. (1985) J. Mol. Biol. 182:191-203), and the Gin/gix system of phage Mu (Maeser and Kahlmann (1991) Mol. Gen. Genet. 230:170-6).

Various assays can be employed in connection with the nucleic acid molecule of certain embodiments herein. In addition to phenotypic observations, the following techniques are useful in detecting the presence of a nucleic acid molecule in a plant cell. For example, the presence of the molecule can be determined by using a primer or probe of the sequence, an ELISA assay to detect an encoded protein, a Western blot to detect the protein, or a Northern or Southern blot to detect RNA or DNA. Additional techniques, such as in situ hybridization, enzyme staining, and immunostaining, also may be used to detect the presence or expression of a recombinant construct in specific plant organs and tissues.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with $^{32}P$ (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with $^{32}P$ (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

Nucleic acids herein, or segments thereof, may be used to design primers for PCR amplification. In performing PCR amplification, a certain degree of mismatch can be tolerated between primer and template. Mutations, insertions, and deletions can be produced in a given primer by methods known to an ordinarily skilled artisan.

Hydrolysis probe assay, otherwise known as TAQMAN® (Life Technologies, Foster City, Calif.), is another method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

VI. Plants

Some embodiments herein provide transgenic plants comprising at least one nucleic acid comprising a target site for at least one sRNA molecule, such as may be regenerated from stably transformed plant cells or tissues, or may be produced by introgression of such a nucleic acid from a donor line. Such plants may be used or cultivated in any manner, wherein presence of the transforming polynucleotide(s) of interest is desirable. Accordingly, transgenic plants may be engineered to, inter alia, have one or more desired traits, by transformation, and then may be cropped and cultivated by any method known to those of skill in the art. Particular embodiments herein provide parts, cells, and/or tissues of such transgenic plants. Plant parts, without limitation, include seed, endosperm, ovule and pollen. In some embodiments, the plant part is seed tissue including seed coat, embryo, cotyledon, endosperm, radicle, hypocotyl, or epicotyl.

Representative, non-limiting example plants include *Arabidopsis*; field crops (e.g. alfalfa, barley, bean, clover, corn, cotton, flax, lentils, maize, pea, rape (e.g., canola), rice, rye, safflower, sorghum, soybean, sunflower, tobacco, and wheat); vegetable crops (e.g., asparagus, beet, *Brassica*, broccoli, Brussels sprouts, cabbage, carrot, cauliflower, celery, cucumber (cucurbits), eggplant, lettuce, mustard, onion, pepper, potato, pumpkin, radish, spinach, squash, taro, tomato, and zucchini); fruit and nut crops (e.g., almond, apple, apricot, banana, blackberry, blueberry, cacao, cassava, cherry, citrus, coconut, cranberry, date, hazelnut, grape, grapefruit, guava, kiwi, lemon, lime, mango, melon, nectarine, orange, *papaya*, passion fruit, peach, peanut, pear, pineapple, pistachio, plum, raspberry, strawberry, tangerine, walnut, and watermelon); tree woods and ornamentals (e.g., alder, ash, aspen, azalea, birch, boxwood, *camellia*, carnation, *chrysanthemum*, elm, fir, ivy, jasmine, juniper, oak, palm, poplar, pine, redwood, *rhododendron*, rose, and rubber).

To confirm the presence of a transforming polynucleotide(s) of interest in a regenerating plant, a variety of assays may be performed. Such assays include, for example and without limitation: biochemical assays, such as detecting the presence of a protein product, e.g., by immunological means (ELISA and/or Western blots) or by enzymatic function; plant part assays (e.g., leaf or root assays); and analysis of the phenotype of the plant.

There are numerous steps in the development of any novel, desirable plant germplasm, which may begin with the generation of a transgenic crop plant. In some embodiments, a transgenic plant comprising at least one nucleic acid comprising a target site for at least one sRNA molecule (e.g., a male sterile plant) may be used in a plant breeding and/or germplasm development program.

Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

The choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In embodiments herein, a transgene comprising a target site for at least one sRNA molecule may be introduced into a plant germplasm, for example, to develop novel inbred lines that are characterized by the tissue-specific expression of the transgene, under the control of the sRNA molecule. A particular advantage of such a development program may be that the generality of the RNAi pathway results in a higher penetrance of the transgenic phenotype than would otherwise be attainable, for example, by other control mechanisms.

The following examples are provided to illustrate certain particular features and/or embodiments. The examples should not be construed to limit the disclosure to the particular features or embodiments exemplified.

Examples

Example 1: Tissue-Specific sRNAs

Many plant miRNAs have a distinct developmental and tissue-specific expression pattern. For example, *Arabidopsis thaliana* miR171 (previously known as miR39) accumulates predominantly in inflorescence tissues. miR171 is produced from an intergenic region in chromosome III and functionally interacts with mRNA targets encoding several members of the Scarecrow-like (SCL) family of putative transcription factors. Llave et al. (2002) Science 297: 2053-6. The interaction results in tissue-specific cleavage of target mRNAs within the region of complementarity between miR171 and a native gene mRNA. Transgene mRNAs carrying the target site sequence are also recognized and cleaved.

Small RNA Library Construction and Sequencing:

Small RNA library construction was carried out using Illumina's TruSeq Small RNA sample preparation kit according to the manufacturer's recommendations. Briefly, RNA 3' and RNA 5' adapters were sequentially ligated ontol μg of high-quality purified Small RNA sample using truncated T4 RNA Ligase 2 and T4 RNA Ligase respectively. The small RNA fragments were then copied into first strand cDNA using SuperScript II reverse transcriptase. The cDNA was converted into double stranded cDNA (ds cDNA) with PCR using two primers that respectively anneal to the ends of 3' and 5' adapters. This process selectively enriches those fragments that have adapter molecules on both ends. The amplified cDNA construct is then purified on a 6% PAGE gel, normalized to 2 nM concentration, denatured with sodium hydroxide, and diluted in hybridization buffer for loading onto a Hiseq flow cell. Cluster generation, primer hybridization and sequencing reactions were carried out according to Illumina's recommended protocol.

Data regarding miRNA expression of miR3522 (SEQ ID NO: 1) and miR1512 (SEQ ID NO:3) are shown in Table 1. The data demonstrate that miR1512 is expressed at high levels in the seed and seed coat, with medium expression in root, and very low expression in leaves and other vegetative tissue, whereas miR3522 is expressed at high or medium levels in all tissues examined except the root tissue. Given the variation in expression among different soybean tissues, miR1512 and miR3522 recognition sites were selected to exemplify tissue-specific transgene expression modulation in a dicot plant.

Table 1. miRNA microarray expression profiling of miR1512 and miR3522 in soybean tissues. Numbers represent relative expression levels.

TABLE 1

| miRNA | Construct | Root tip | Root | Hypocotyl | Leaf | Stem | Flower | Pod | 3 mm seed | 5 mm seed | Pods from 5 mm seeds | Cotyledons | Seed coat | Embryo axis |
|---|---|---|---|---|---|---|---|---|---|---|---|---|---|---|
| miR1512 | 113183 | 3118 | 0 | 0 | 0 | 15 | 79 | 1854 | 10427 | 183 | 23938 | 70 | 13532 | 20 |
| miR3522 | 113177 | 649 | 399 | 1310 | 15350 | 3180 | 18509 | 405 | 8958 | 30139 | 1351 | 25265 | 2551 | 3200 |

Example 2: Plant Transformation Vectors

In order to investigate whether endogenous miRNA molecules can be used to confer modulation of transgene expression, the following nucleic acid constructs were engineered and produced.

Plant Transformation Constructs. All constructs contain the pat gene expression cassette, which contains the CsVMV promoter v2 (promoter and 5' untranslated region derived from the Cassava Vein Mosaic virus; Verdaguer, B.; de Kochko, A.; Beachy, R. N.; Fauquet, C. (1996), Isolation and expression in transgenic tobacco and rice plants, of the cassava vein mosaic virus (CVMV) promoter. Plant Molecular Biology, 31(6): 1129-1139) and the *Zea mays* Lipase 3'UTR (labeled as "Zm Lip3 3'UTR"), pat v6 coding sequence (synthetic, plant-optimized version of phosphinothricin acetyl transferase (pat) gene, isolated from *Streptomyces viridochromogenes*, encoding a protein that confers resistance to inhibitors of glutamine synthetase comprising phophinothricin, glufosinate, and bialaphos. Wohlleben, W.; Arnold, W.; Broer, I.; Hillemann, D.; Strauch, E.; Puehler, A. Nucleotide sequence of the phosphinothricin N-acetyltransferase gene from *Streptomyces viridochromogenes* Tu494 and its expression in *Nicotiana tabacum*. Gene (1988), 70(1): 25-37), and AtuORF1 3' UTR v3 (3' untranslated region (UTR) comprising the transcriptional terminator and polyadenylation site of open reading frame 1 (ORF1) of *Agrobacterium tumefaciens* pTi15955. Barker, R. F.; Idler, K. B.; Thompson, D. V.; Kemp, J. D. Nucleotide sequence of the T-DNA region from the *Agrobacterium tumefaciens* octopine Ti plasmid pTi15955. Plant Molecular Biology (1983), 2(6): 335-50). pDAB113181 contains AAD-12 expression cassette comprising the ATUBI401.8 promoter (promoter, 5' untranslated region and intron from the *Arabidopsis thaliana* polyubiquitin 10 (UBQ10) gene, Norris, S. R.; Meyer, S. E.; Callis, J. (1993). The intron of *Arabidopsis thaliana* polyubiquitin genes is conserved in location and is a quantitative determinant of chimeric gene expression. Plant Molecular Biology, 21(5): 895-906), AAD-12 v1 (synthetic, plant-optimized version of an aryloxyalkanoate dioxygenase gene from *Delftia acidovorans* encoding an enzyme with alpha ketoglutarate-dependent dioxygenase activity which results in metabolic inactivation of the herbicide(s) on which it has enzymatic activity, WO2007/053482), and the AtuORF23 3' UTR v1(3' untranslated region (UTR) comprising the transcriptional terminator and polyadenylation site of open reading frame 23 (ORF23) of *Agrobacterium tumefaciens* pTi15955. Barker, R. F.; Idler, K. B.; Thompson, D. V.; Kemp, J. D. (1983), Nucleotide sequence of the T-DNA region from the *Agrobacterium tumefaciens* octopine Ti plasmid pTi15955. Plant Molecular Biology, 2(6): 335-50). pDAB113177 contains AAD-12 expression cassette comprising the ATUBI401.8 promoter (promoter, 5' untranslated region and intron from the *Arabidopsis thaliana* polyubiquitin 10 (UBQ10) gene, Norris, S. R.; Meyer, S. E.; Callis, J. (1993). The intron of *Arabidopsis thaliana* polyubiquitin genes is conserved in location and is a quantitative determinant of chimeric gene expression. Plant Molecular Biology, 21(5): 895-906), AAD-12 v1 (synthetic, plant-optimized version of an aryloxyalkanoate dioxygenase gene from *Delftia acidovorans* encoding an enzyme with an alpha ketoglutarate-dependent dioxygenase activity which results in metabolic inactivation of the herbicide(s) on which it has enzymatic activity, WO2007/053482), and the AtuORF23 3' UTR v1 (3' untranslated region (UTR) comprising the transcriptional terminator and polyadenylation site of open reading frame 23 (ORF23) of *Agrobacterium tumefaciens* pTi15955. Barker, R. F.; Idler, K. B.; Thompson, D. V.; Kemp, J. D. Nucleotide sequence of the T-DNA region from the *Agrobacterium tumefaciens* octopine Ti plasmid pTi15955. Plant Molecular Biology (1983), 2(6): 335-50). The miRNA target site HTRNA15975.1 (SEQ ID NO:2) for miRNA3522 (SEQ ID NO: 1) was added between AAD-12 v1 and AtuORF23 3' UTR v1. pDAB113183 contains AAD-12 expression cassette comprising the ATUBI401.8 promoter (promoter, 5' untranslated region and intron from the *Arabidopsis thaliana* polyubiquitin 10 (UBQ10) gene, Norris, S. R.; Meyer, S. E.; Callis, J. (1993), The intron of *Arabidopsis thaliana* polyubiquitin genes is conserved in location and is a quantitative determinant of chimeric gene expression. Plant Molecular Biology, 21(5): 895-906), AAD-12 v1 (synthetic, plant-optimized version of an aryloxyalkanoate dioxygenase gene from *Delftia acidovorans* encoding an enzyme with an alpha ketoglutarate-dependent dioxygenase activity which results in metabolic inactivation of the herbicide(s) on which it has enzymatic activity, WO2007/053482), and the AtuORF23 3' UTR v1(3' untranslated region (UTR) comprising the transcriptional terminator and polyadenylation site of open reading frame 23 (ORF23) of *Agrobacterium tumefaciens* pTi15955. Barker, R. F.; Idler, K. B.; Thompson, D. V.; Kemp, J. D. Nucleotide sequence of the T-DNA region from the *Agrobacterium tumefaciens* octopine Ti plasmid pTi15955. Plant Molecular Biology (1983), 2(6): 335-50). The miRNA target site HTRNA17596.1 (SEQ ID NO:2) for miRNA1512 (SEQ ID NO:4) was added between AAD-12 v1 and AtuORF23 3' UTR v1. AAD-12 expression cassette comprising the ATUBI401.8 promoter, AAD-12 v1 coding sequence, miR1512 target site, and the AtuORF23 3' UTR v1.

miRNA target sites: The miRNA target site sequences for miR1512 and miR3522 were designed to bind miRNA at the 3' end of the coding region.

TABLE 2

Exemplary miRNA target sites.

| | | |
|---|---|---|
| SEQ ID NO: 2 | TCAGCTGCTCATTTGGTCTCA | miRNA3522 |
| SEQ ID NO: 4 | ATGCTCTAAGAATGTTCAGTTA | miRNA1512 |

Gateway® (INVITROGEN) entry vectors were constructed by standard molecular cloning methods, and were used to create plant transformation vectors pDAB113181, pDAB113177, and pDAB113183.

The structures of all plasmids were confirmed by restriction enzyme digests and determinations of the DNA base sequences of relevant regions were confirmed by standard molecular biological techniques.

Example 3: Stable Expression in Soybean

*Agrobacterium*-mediated transformation was used to stably integrate a chimeric gene into the plant genome, and thus generate transgenic soybean cells, tissues, and plants that produce AAD12 mRNAs having miRNA target sites within the mRNA. Control tissues having no miRNA target sites in the AAD1 mRNA were also produced.

*Agrobacterium*-Mediated Plant Transformation:

*Agrobacterium*-mediated transformation of soybean (*Glycine max* cv., Maverick) was performed via the split-seed explant with partial embryo axis soybean transformation protocol described in US 2014/0173774 A1. After transformation, co-cultivation of explants was carried out for 5 days. The explants were then washed in liquid Shoot Induction (SI) medium for about 5 to 10 minutes and cultured onto Shoot Induction-I (SI-I) medium. After 2 weeks of culture at 24° C. with an 18 hour photoperiod, the explants were transferred to the Shoot Induction-II (SI-II) medium supplemented with 6 mg/L glufosinate. After 2 weeks on SI-II medium, the cotyledons were removed from the explants, a flush shoot pad was excised by making a cut at the base of the cotyledon, and the isolated shoot was transferred to the Shoot Elongation (SE) medium. The cultures were transferred to fresh SE medium every two weeks. Lighting sources were provided with an illumination of 80-90 moles $s^{-1}$ $m^{-2}$ for the transformed tissues during shoot induction and shoot elongation. The elongated shoots were dipped in 1 mg/L indole 3-butyric acid (IBA) for about 1 to 3 minutes to promote rooting prior to transferring of the isolated shoots to rooting medium (MS salts, B5 vitamins, 28 mg/L ferrous sulphate, 38 mg/L Na$_2$EDTA, 20 g/L sucrose and 0.59 g/L MES, 50 mg/L asparagine, 100 mg/L L-pyroglutamic acid, and 7 g/L NOBLE™ agar, pH 5.6) in phyta trays. Following culturing in the rooting medium at 24° C., with an 18 hour photoperiod, for 1-2 weeks, the soybean shoots that produced healthy, viable roots were transferred to soil. The soybean shoots comprising healthy, viable roots were placed in soil which was contained in an open plastic sundae cup. The plastic sundae cups containing the transferred soybean shoots comprising roots were placed in a CONVIRON™ for acclimatization of soybean plantlets. The rooted soybean plantlets were acclimated in the open sundae cups for several weeks before the plantlets were transferred to the greenhouse and grown to maturity for T1 seed production.

T1 seed generated from self-pollination of single copy T0 events were planted in an artificial soil mix (MetroMix 360™) contained in 4-inch square pots. The T1 generation is a segregating population; to distinguish transformed events from null individuals, the T1 population received a foliar application of 411 g active ingredient (ai)/ha glufosinate ammonium (LIBERTY 280) when plants reached the 1$^{st}$ trifoliate leaf stage. Four days after application (DAA), survivors were sampled for molecular analysis to determine zygosity and confirm aad12 copy number.

For each event, 8 homozygous and 8 hemizygous plants were sampled for transcript and protein analyses, and the following day (3$^d$ trifoliate stage), half of the plants received a foliar application of 2240 g acid equivalent (ae)/ha 2,4-D dimethylamine (DMA) salt (WEEDAR 64). The remaining plants received no spray application. Some plants were also sprayed with deionized water as a sprayer application control. In addition to the transformed events, the soybean variety, 'Maverick', was included in each treatment as a non-transformed control.

Foliar applications were made with a Mandel track sprayer set to deliver a spray solution at 187 L/ha to a spray area of 0.503 m$^2$ using an 8002E nozzle and a spray height of 18 inches above the plant canopy. Plant response to the 2,4-D application was evaluated at 1, 7, and 14 days after application (DAA). Data were collected by assessment of visual injury and/or growth reduction as compared to untreated controls on a scale of 0% to 100% with 0% corresponding to no injury or growth reduction and 100% corresponding to complete plant death. Plants were maintained at 28° C./25° C. (day/night) under a 14 h photoperiod and subirrigated with water or fertilizer as needed.

Example 4: Biochemical and Molecular Analyses of Transgenic Soybean Tissues

Protein extraction from soybean leaf: Two 6 mm diameter leaf samples were stored in a 96 well cluster tube rack at −80° C. until the day of analysis. Two DAISY™ steel BB's and 200 µl of extraction buffer (PBS solution containing 0.05% of Tween 20, 5 µl/ml of Sigma protease inhibitors catalog number 9599, and 0.75% Ovabumin Sigma catalog number A-5503) were added to each tube. The samples were milled in a KLECKO™ tissue pulverizer for 3 minutes, on the maximum setting. Samples were centrifuged at 3,000×g for 5 minutes; 100 µl of the supernatant was transferred to an empty sample tube. Another 100 µl of extraction buffer was added to the plant sample and bead milled for 3 additional minutes, centrifuged, and 100 µl of this extract was combined with the first 100 µl. The combined supernatants were mixed and analyzed the same day as the extraction.

ELISA Quantification of AAD12 Protein:

Enzyme Linked Immunosorbant Assays (ELISAs) were used to measure the production of AAD12 proteins in soybean leaf. AAD12 protein was quantified using a ENVIROLOGIX™ (catalog number AP018) kit using a Dow AgroSciences produced AAD12 purified protein as the standard. The standard curve ranged from 200 ng/ml to 3.1 ng/ml. The ELISAs were performed using the reagents and instructions essentially as provided by the suppliers.

Total RNA extraction for sRNA sequencing Total RNA was isolated using Plant/Fungi Total RNA Purification Kit (Norgen #25800). The standard manufacturer's protocol was followed with ~30 mg of the ground tissues as starting material including the on-column DNase treatment step. The concentration and quality of RNA for each sample was determined by UV spectrometry (Nanodrop ND-1000 spectrophotometer). Approximately 1 ug of total RNA was used for sRNA library preparation.

Hydrolysis Probe qPCR for Copy Number Analysis:

Various types of molecular analyses were employed to screen for low copy, simple events. Leaf tissue was collected from rooted putative transgenic plants before transplanting to soil. DNA was extracted with a QIAGEN MAGATTRACT™ kit using THERMO FISHER KINGFISHER™ magnetic particle processors and the supplier's recommended protocols. Integrated transgene copy number analysis was performed using specific Hydrolysis Probe assays for the AAD12 and PAT genes. In addition, contamination by inadvertent integration of the binary vector plasmid backbone was detected by a Hydrolysis Probe assay specific for the Spectinomycin resistance gene (Spec) borne on the binary vector backbone. Hydrolysis Probe assays for endogenous soybean genes GSM116; (GenBank™ Accession No. AK286292.1) and Actin (GENBANK Accession No. V00450.1) were developed as internal reference standards. Table 3 lists the oligonucleotide sequences of the Hydrolysis Probe assay components (synthesized by INTEGRATED DNA TECHNOLOGIES, Coralville, Iowa). Biplex Hydrolysis Probe PCR reactions were set up according to Table 4 with about 10 ng DNA, and assay conditions are presented in Table 5.

TABLE 3

List of forward and reverse nucleotide primers and fluorescent probes used for transgene copy number and relative expression detection.

| Gene Detected | Oligonucleotide | Sequence |
|---|---|---|
| AAD12 | AAD12_F | AACCCGTGCTCTTGTTC (SEQ ID NO: 9) |
|  | AAD12_R | GGATGCACCTTGACCAAT (SEQ ID NO: 10) |
|  | AAD12_P (FAM* Probe) | CAGGCCGGGTCAGCCT (SEQ ID NO: 11) |
| PAT | PAT_F | ACAAGAGTGGATTGATGATCTAGAGAGGT (SEQ ID NO: 12) |
|  | PAT_R | CTTTGATGCCTATGTGACACGTAAACAGT (SEQ ID NO: 13) |
|  | PAT_FamP (FAM Probe) | GGTGTTGTGGCTGGTATTGCTTACGCTGG (SEQ ID NO: 14) |
| Spec | Spec_F | CGCCGAAGTATCGACTCAACT (SEQ ID NO: 15) |
|  | Spec_R | GCAACGTCGGTTCGAGATG (SEQ ID NO: 16) |
|  | Spec_P (FAM Probe) | TCAGAGGTAGTTGGCGTCATCGAG (SEQ ID NO: 17) |
| Soybean GMS116 | GMS116_F | GTAATATGGGCTCAGAGGAATGGT (SEQ ID NO: 18) |
|  | GMS116_R | ATGGAGAAGAACATTGGAATTGC (SEQ ID NO: 19) |
|  | GMS116_P (HEX* Probe) | CCATGGCCCGGTACCATCTGGTC (SEQ ID NO: 20) |
| Soybean Actin | Soy Actin_F | GTGACTCACACCATCACCAGAGT (SEQ ID NO: 21) |
|  | Soy Actin_F | ATCCAGGCTGTCCTCTCCCTATA (SEQ ID NO: 22) |
|  | Soy Actin_P* (VIC ® Probe) | CAATACCAGTTGTGCGACC (SEQ ID NO: 23) |

*FAM = 6-Carboxy Fluorescein Amidite; HEX = Hexachlorofluorescein

TABLE 4

Hydrolysis Probe PCR Mixture for Transgene DNA Copy Number Analysis.

| Reaction Component | μL | Final Concentration |
|---|---|---|
| Water | 0.5 |  |
| PVP (10%) | 0.1 | 0.1% |
| ROCHE 2X Master Mix | 5 | 1X |
| Transgene Forward Primer (10 μM) | 0.4 | 0.4 μM |
| Transgene Reverse Primer (10 μM) | 0.4 | 0.4 μM |
| Transgene Probe (5 μM) | 0.4 | 0.2 μM |
| GMS116 Forward Primer (10 μM) | 0.4 | 0.4 μM |
| GMS116 Reverse Primer (10 μM) | 0.4 | 0.4 μM |
| GMS116 Probe (5 μM) | 0.4 | 0.2 μM |

TABLE 5

Thermocycler Conditions for Hydrolysis Probe PCR Amplification.

| PCR Steps | Temp (° C.) | Time | No. cycles |
|---|---|---|---|
| Denature/Activation | 95 | 10 min | 1 |
| Denature | 95 | 10 sec | 40 |
| Anneal/Extend | 60 | 35 sec |  |
| Acquire | 72 | 1 sec |  |
| Cool | 40 | 10 sec | 1 |

For amplification, LIGHTCYCLER480 Probes Master mix (ROCHE APPLIED SCIENCE, Indianapolis, Ind.) was prepared at 1× final concentration in a 10 μL volume multiplex reaction containing 0.1% PVP, 0.4 μM of each primer, and 0.2 μM of each probe. The FAM (6-Carboxy Fluorescein Amidite) fluorescent moiety was excited at 465 nm, and fluorescence was measured at 510 nm. The corresponding values for the HEX (hexachlorofluorescein) fluorescent moiety were 533 nm and 580 nm, and for VIC® the values were 538 nm and 554 nm. The level of fluorescence generated for each reaction was analyzed using the ROCHE LIGHTCYCLER®480 Real-Time PCR system according to the manufacturer's recommendations. Transgene copy number was determined by comparison of LIGHTCYCLER®480 outputs of Target/Reference gene values for unknown samples to Target/Reference gene values of known copy number standards (1-Copy representing hemizygous plants, 2-Copy representing homozygous plants).

Cp scores; i.e., the point at which the florescence signal crosses the background threshold using the fit points algorithm (LIGHTCYCLER® software release 1.5), and the Relative Quant module (based on the ΔΔCt method), were used to perform the analysis of real time PCR data.

In the LIGHTCYCLER® Fit Points Algorithm software, a graph of the data was made by plotting the logarithm of the input DNA template concentration against the measured Cp values. The slope of the curve is a desired comparison parameter; therefore the initial log input number can be an arbitrary starting point on the curve, with the caveat that the arbitrary concentration values used for input DNA template are representative of the actual serial dilution used. For example, for a 10-fold serial dilution series, the actual inputs concentrations may be 1000, 100, 10, etc., for which points the LC480 Fit Points Algorithm software plots 3, 2, 1, etc. as the logarithms of the inputs. Using a linear regression, the resulting best fit of this line (input log vs Cp) was then used to estimate a slope (m) from an equation of the form y=mx+b. There is an inverse relationship between the starting template amount and Cp value, and therefore the slope (m) is always negative.

A perfect (i.e., 100% efficient) PCR reaction doubles the total template every cycle. PCR efficiency (Eff) is calculated as:

$$Eff=10e^{(-1/m)}$$

Thus, the slope (m) of the graph of log input vs Cp will be −3.3219 for a perfectly efficient reaction (whose efficiency is defined as 2.00).

In other words, a 100% efficient PCR reaction is defined by:

$$2.0=10e^{(-1/-3.3219)}$$

The LC480 Fit Points Algorithm software reports the efficiency value by the first formula. So a 99% efficient reaction has an Eff value of 1.99, rather than 0.99.

To express this as a percent efficiency, subtract 1 from this value and multiply by 100. Or, $$\% \text{ Eff}=[(10e^{(-1/m)-1})]\times 100$$

AAD12 relative transcript analysis: Quantitative Hydrolysis Probe PCR was also used to detect the relative levels of AAD12 transcript. Leaf tissue was collected at the V4 stage while cotyledon and seed coat tissue was extracted from immature seed. Approximately 500 ng total RNA (extracted with a KINGFISHER™ total RNA Kit; THERMO FISHER SCIENTIFIC) was used for cDNA synthesis using a high capacity cDNA synthesis kit (INVITROGEN) and random primer T20VN (TTTTTTTTTTTTTTTTTTTTVN; where V is A, C, or G, and N is A, C, G, or T/U). Typically, a 20 µL reaction contained 2.5 U/µL MULTISCRIBE™ reverse transcriptase, 200 nM T20VN oligonucleotide, and 4 mM dNTPs. The reaction was initiated by incubation for 10 minutes at 25° C., then synthesis was performed for 120 minutes at 37° C. and inactivated by 5 minutes at 85° C.

Newly-synthesized cDNA was used for PCR amplification. Hydrolysis Probe qPCR set up, running conditions, and signal capture were the same as given above for DNA copy number analyses. AAD12 expression data were calculated using 2-ΔΔCt relative to the level of Actin.

Example 5: miRNA3522 Target Site-Mediated Optimization of AAD12 mRNA Expression in Different Tissues Sampled from T1 Transgenic Soybean Plants Transgenic soybean plants were produced wherein the accumulation of an AAD12 mRNA comprising a miRNA target site was limited by miRNA3522 cleavage in tissues or cells comprising the leaf, stem, flower, seed, cotyledons, seed coat, embryo, or other cells. Micro RNA expression profiling disclosed in Table 1 shows that miR3522 is not specifically expressed in the root tissue, but rather is expressed at medium to high levels in a majority of the above ground tissues of the soybean plant.

Figure 5:
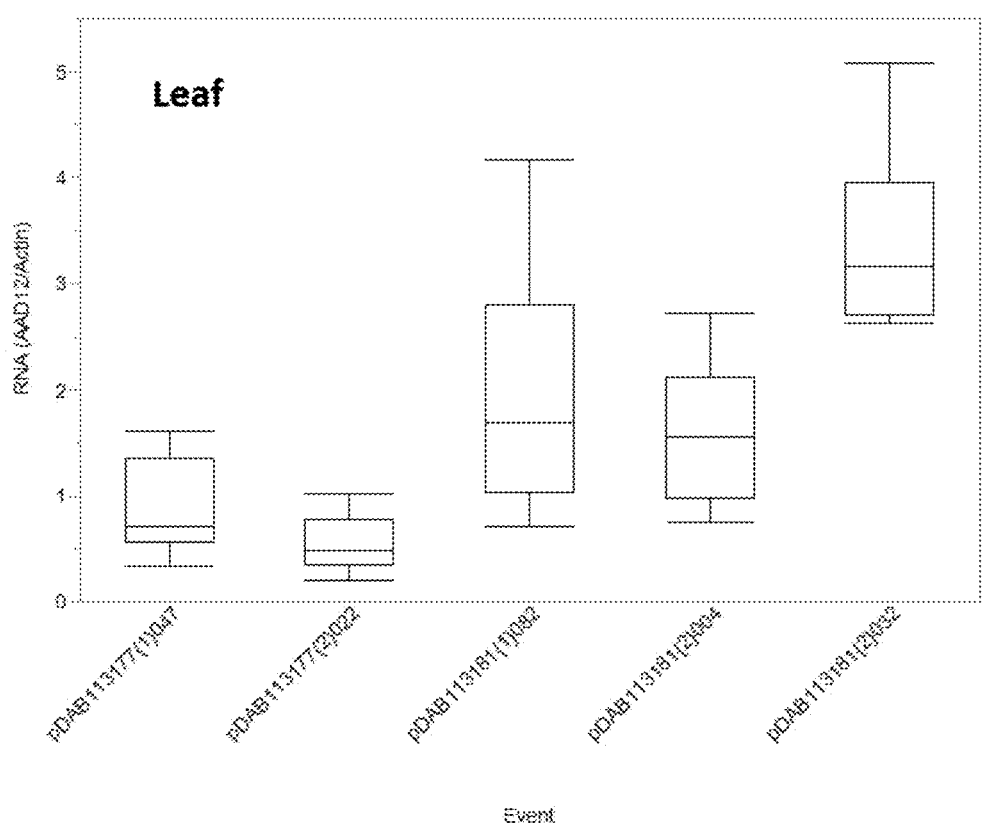
FIG. 5 is a graph of data showing the modulation of transcript expression of aad12 in leaf using miRNA3522 target site.
Figure 6:
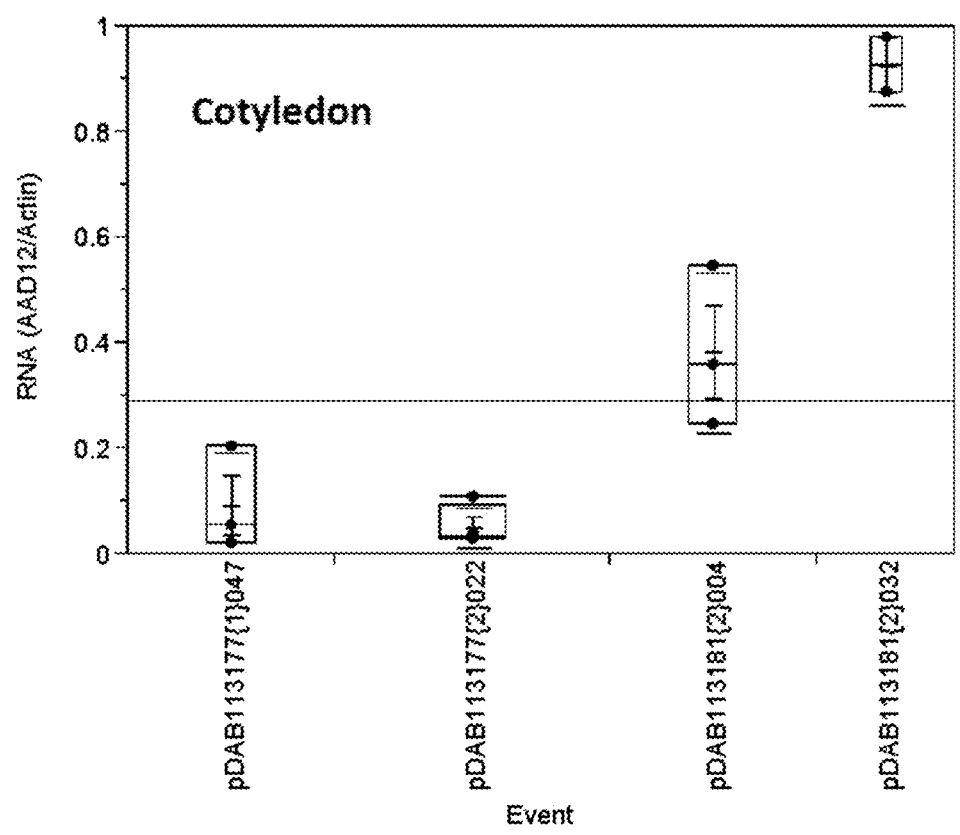
FIG. 6 is a graph of data showing the modulation of transcript expression of aad12 in cotyledon using miRNA3522 target site.
Figure 7:
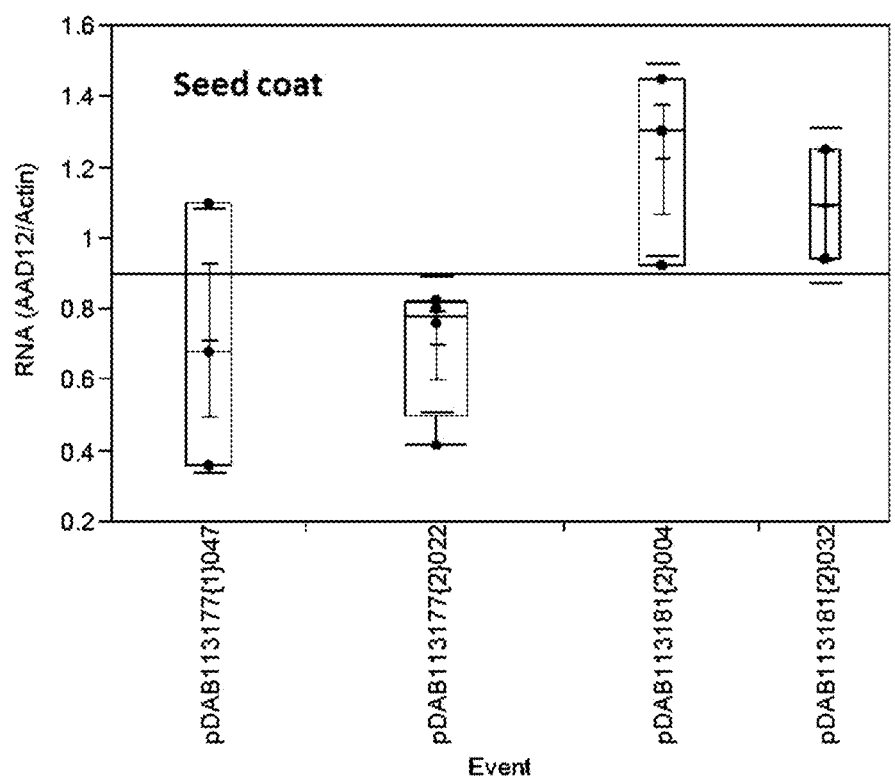
FIG. 7 is a graph of data showing the modulation of transcript expression of aad12 in seed coat using miRNA3522 target site.

More than 15 plants from each single copy transgenic event were analyzed for expression analysis. AAD-12 mRNA levels were calculated relative to the levels of soybean actin mRNA as described in EXAMPLE 4. The data in FIGS. 5, 6, & 7 show that there was tissue-specific effect of miRNA3522 miRNA target sites on AAD12 expression. The accumulation of AAD12 transcript was reduced in leaf, cotyledon and seed coat tissue samples obtained from soybean plants transformed with construct pDAB113177 containing miRNA3522 target site, as compared to the "no miRNA" control plants transformed with pDAB113181. The AAD12 reduction in these plants is due to miR3522 that is present in high abundance in the leaf, seed coat and cotyledon tissue. These results confirm that adding target sites of naturally occurring miRNA in the transgene can be exploited to optimize expression of a transgene in a dicot plant.

Example 6: miRNA1512 Target Site-Mediated Optimization of AAD12 mRNA Expression in Soybean Seed Tissues Transgenic soybean plants were produced wherein the accumulation of an AAD12 mRNA comprising a miRNA target site was limited by miRNA1512 cleavage in tissues or cells comprising the seed, pods, seed coat, and root tip. Micro RNA expression profiling disclosed in Table 1 shows that miR1512 is not specifically expressed in the root, hypocotyl, leaf, stem, flower, and cotyledon but rather is expressed at medium to high levels in seed and seed coat tissues of the soybean plant.

Immunolocalization of AAD12 protein was done to demonstrate the effect of miRNA1512 on expression of AAD12 in seed tissue. Seeds coats were removed from the cotyledons of mature, dry soybean seeds. Seeds were oriented with the hilum down and with the median sagittal plane passing between the left and right cotyledons. The hilum was removed with a single transverse cut just above the hilum. The median coronal section, approximately 1 mm thick, was dissected from the seed, and the coat was removed from the two cotyledon pieces. This region was chosen because it includes both thick (lateral) and thin (dorsal) regions of seed coat in the same piece of tissue. Seed coats and cotyledons of each sample type were placed in scintillation vials and fixed overnight at 4° C. in 4% formaldehyde (in 10 mM phosphate buffered saline [PBS] with 1:10,000 Silwet L-77 [Lehle Seeds, Round Rock, Tex., USA]). Fixative solution was removed the following day, and samples were rinsed briefly with 10 mM PBS solution. Undiluted acetylated bovine serum albumin (BSA-c™, Aurion, Electron Microscopy Sciences, Hatfield, Pa., USA) solution was added and allowed to infiltrate the samples on a rotator at 4° C. for 4 hrs. Samples were again rinsed briefly with 10 mM PBS to remove excess BSA-c™, and then returned to fresh fixative solution for a second overnight fixation in 4% formaldehyde. Samples were briefly rinsed with 10 mm PBS, and dehydrated in a graded ethanol series. Samples were then infiltrated with LR White resin (Polysciences, Warrington, Pa.) and polymerized into acrylic blocks; seed coats and corresponding cotyledons were polymerized together in the same block.

500 nm thick sections were generated for all samples using a DDK histo diamond knife (Delaware Diamond Knives, Inc., Wilmington, Del., USA) on a Leica EM UC 7 ultramicrotome (Leica Microsystems, Buffalo Grove, Ill., USA). Tissue sections were stretched and dried onto Fisherbrand™ SuperFrost™ Plus slides (Thermo Fisher Scientific, Pittsburgh, Pa., USA). Two sections (technical replicates) were generated for each sample type. Sections were immunolabeled with a custom mouse monoclonal antibody to the AAD12 protein at a concentration of 1:2000 in Da Vinci Green antibody diluent (Biocare Medical, Concord, Calif., USA), amplified with a two part probe-polymer HRP secondary antibody system (Biocare Medical, Concord, Calif., USA), and signal was detected with an enzymatic deposition of silver (EnzMet™ Silver, Nanoprobes, Inc., Yaphank, N.Y., USA).

All steps of the immunolocalization were completed in an opaque humid box (Evergreen Scientific, Vernon, Calif.) at RT. Tissue sections were first blocked with a PBS-BSA (bovine serum albumin)-Tween 20 (10 mM PBS with 1% BSA and 0.1% Tween 20, all reagents from Sigma-Aldrich, St. Louis, Mo., USA) wash solution for 30 min. The wash solution was removed and the primary antibody was added and incubated for 2.5 hrs with constant agitation. After the primary antibody incubation, the sections were washed 3 times for 5 min each with the washing solution. The HRP probe solution was added and incubated for 15 min with agitation, this solution was removed, another 3 washes for 5 min series was completed, then the HRP polymer solution was added and incubated for 15 min. Another 3 washes for 5 min each was completed, and the slides were gently rinsed in deionized water. Slides were allowed to dry to completion at RT prior to addition of the enzymatic silver solution. Briefly, the solution was prepared according to manufacturer's instructions and incubated on the tissue sections for 12 min on the bench at RT without agitation. Silver solution was removed, and slides were thoroughly rinsed in deionized water, then blown dry with compressed air. Slides were then mounted dry with Poly-Mount Xylene (Polysciences, Inc., Warrington, Pa., USA) and Corning brand cover glasses (Thermo Fisher Scientific, Pittsburgh, Pa., USA), weighted on a slide warmer, and cured overnight prior to viewing and imaging. Slides were imaged on a Leica DM5000 upright microscope (Leica Microsystems, Buffalo Grove, Ill., USA) with a Leica DFC 7000T digital camera and Leica Application Suite software (version 4.6).

Figure 8:
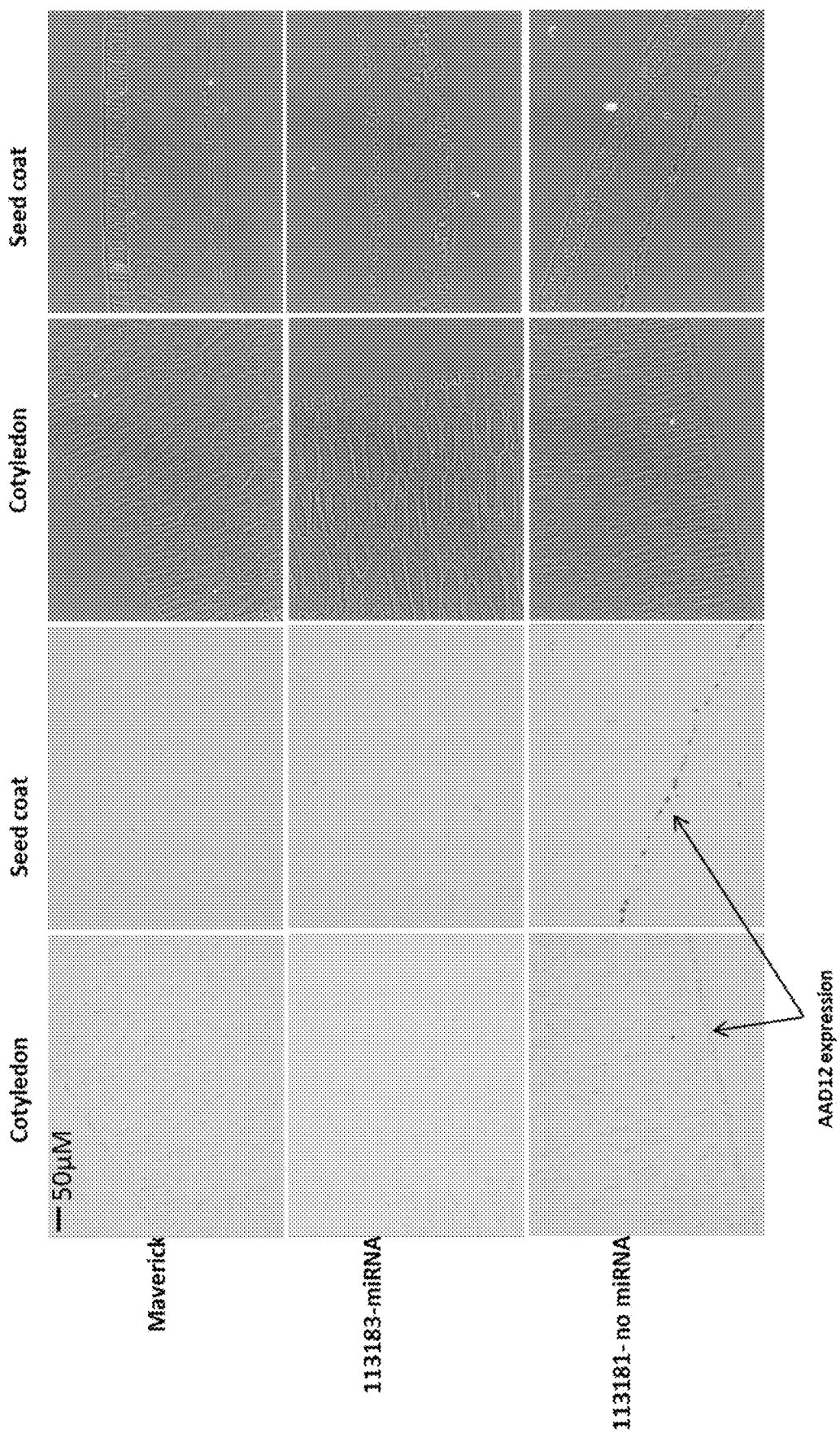
FIG. 8 shows brightfield (left panels) and phase contrast (right panels) microscopy images showing protein expression of aad12 in cotyledon and seed coat.

Brightfield images of the cotyledon and seed coat from the three sample types are shown on the left panels of the FIG. 8, and phase contrast images from the same field of view as each brightfield image are shown on the right. The non-transgenic 'Maverick' cotyledon sections showed a very low level of background silver deposition, and the seed coat sections show essentially no background silver. The sections taken from soybean plants transformed with construct pDAB113183 containing miRNA1512 target site show levels of staining very similar to 'Maverick', indicating below-background levels of AAD12 detected by this method. The sections from "no miRNA" control plants transformed with pDAB113181 showed silver deposition (AAD12 detection) in the cells of the cotyledon, with heavier staining over the epidermal cells; and relatively strong staining primarily of the aleurone layer cells in the seed coat. Scale bar=50 µM.

Figure 9:
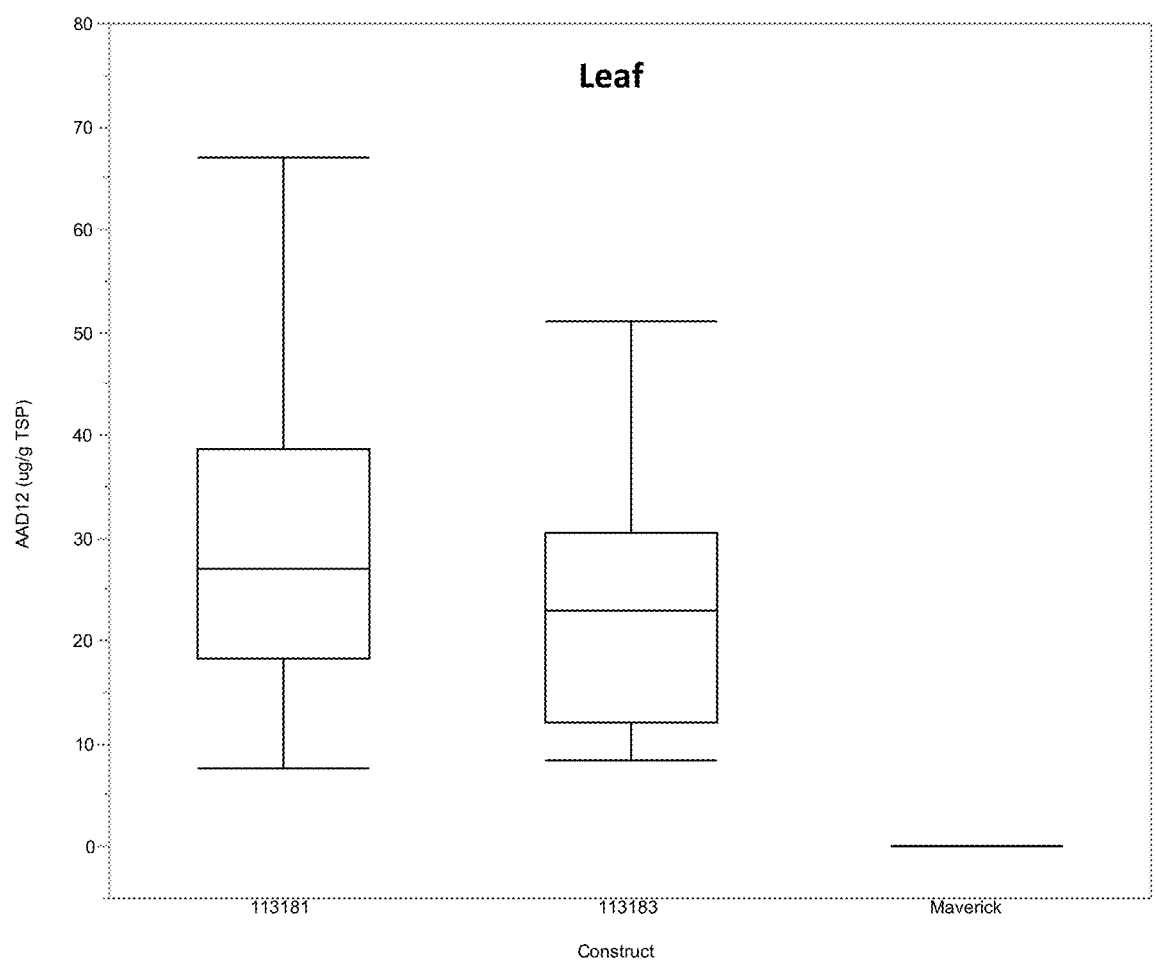
FIG. 9 is a graph of data showing aad12 protein expression in leaf using miRNA3522 target site.

The protein expression analysis of leaf tissue showed no significant change in AAD12 protein in transgenic plants containing miR1512 target site (pDAB113183), when compared to plants producing AAD-12 without any target site (pDAB113181). (FIG. 9).

Figure 10:
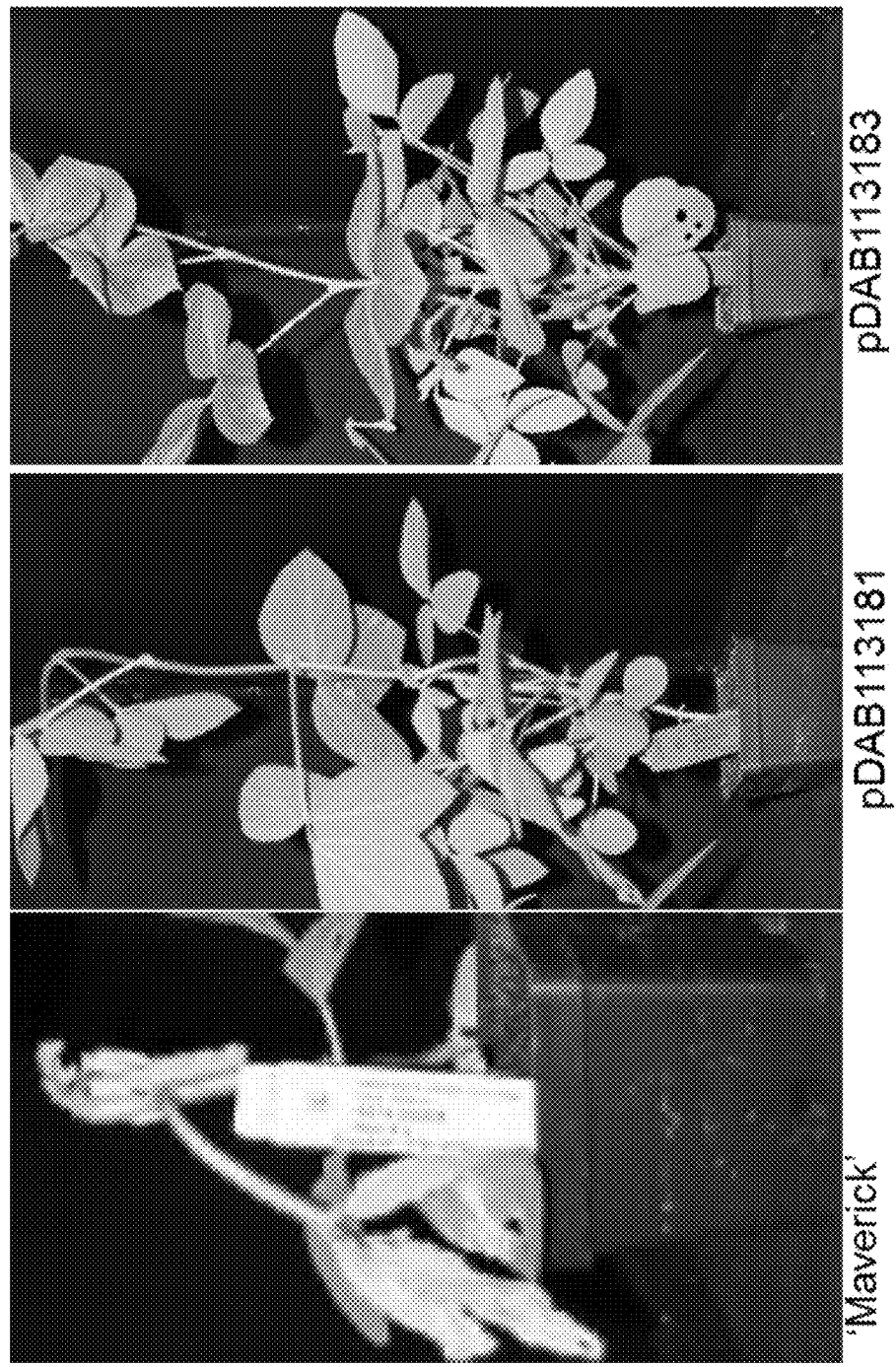
FIG. 10 is a photo showing tolerance of T1 plants to 2,4-D @ 2240 g ae/ha 14 day after spray.

The transgenic plants containing miR1512 target site (pDAB113183) demonstrated robust tolerance to 2,4-D application. Unlike non-transgenic control 'Maverick' plants, both pDAB113181 and pDAB113183 did not show any injury after 2,4-D application (FIG. 10).

These results confirm that desired and precise regulation of expression of one or more transgenes can be obtained by adding selected target sites of native miRNA to the transgene sequence in a tissue-specific, tissue-preferred manner, or cell type-specific manner, depending on the target site selected.

What is claimed is:

1. A nucleic acid expression cassette comprising a gene of interest, a plant promoter operably linked to the gene of interest, and a target site, wherein the target site comprises SEQ ID NO:4, for at least one sRNA molecule present in a dicot plant.

2. The expression cassette of claim 1, wherein the gene of interest is an agronomic trait gene, an insect resistance gene, an herbicide tolerance gene, a non-coding RNA gene, or a selectable marker gene.

3. The expression cassette of claim 1, wherein the target site is between about 21 and about 25 nucleotides in length.

4. The expression cassette of claim 1, wherein the dicot plant is selected from the group consisting of *Arabidopsis*, soybean, rapeseed, cotton, and tobacco.

5. A transgenic plant cell comprising the expression cassette of claim 1, wherein the gene of interest is heterologous to the plant cell, and wherein the at least one sRNA molecule is an endogenous sRNA of the plant cell.

6. The transgenic plant cell of claim 5, wherein the endogenous sRNA is expressed in the plant in a tissue-specific, tissue-preferred, or cell type-specific manner.

7. A transgenic plant tissue, plant part, or plant, comprising the transgenic plant cell of claim 5.

8. The transgenic plant tissue, plant part, or plant of claim 7, wherein the endogenous sRNA is expressed predominantly in seed tissue.

9. The transgenic plant tissue, plant part, or plant of claim 8, wherein the sRNA is SEQ ID NO:3.

10. The transgenic plant tissue, plant part, or plant of claim 9, wherein the gene of interest is an herbicide tolerance gene, and wherein expression of the herbicide tolerance gene is downregulated in seed tissue.

11. The transgenic plant tissue, plant part, or plant of claim 7, wherein the target site is modified for partial or complete downregulation of the gene of interest.

12. A method for producing a transgenic plant cell, the method comprising:
providing a nucleic acid expression cassette comprising an herbicide tolerance gene, a plant promoter operably linked to the gene, and a target site, wherein the target site comprises SEQ ID NO:4, for at least one sRNA molecule; and
transforming a plant cell with the expression cassette, wherein the plant cell expresses the sRNA.

13. The method of claim 12, wherein the sRNA hybridizes to mRNA transcribed from the herbicide tolerance gene and thereby reduces the expression of the herbicide tolerance gene.

14. The method of claim 12, wherein the sRNA is an endogenous sRNA that is expressed in the plant cell in a tissue-preferred, tissue-specific, or cell type-specific manner.

15. The method of claim 12, wherein the sRNA is SEQ ID NO:3.

16. The method of claim 12, wherein the sRNA is encoded by a polynucleotide that is operably linked to a non-constitutive promoter in the genome of the plant cell.

17. The method according to claim 16, wherein the non-constitutive promoter is a tissue-preferred, tissue-specific, or cell type-specific.

18. The method according to claim 16, wherein the non-constitutive promoter is a tissue-specific promoter.

19. The method according to claim 18, wherein the tissue-specific promoter initiates transcription selectively in vegetative tissue.

20. A plant tissue comprising a plant cell produced by the method according to claim 12.

21. A plant comprising the plant tissue of claim 20.

22. A method for producing a transgenic plant cell, the method comprising:
providing a nucleic acid expression cassette comprising a gene of interest and a target site of a sRNA molecule, wherein the target site comprises SEQ ID NO:4;
providing a plant cell, wherein the sRNA is expressed predominantly in seed tissue; and
transforming the plant cell with the expression cassette.

23. The method of claim 22, wherein the sRNA is SEQ ID NO:3.

24. A method for inhibiting expression of a gene of interest in a plant, comprising growing a plant comprising a nucleic acid expression cassette comprising a gene of interest, a plant promoter operably linked to the gene of interest, and a target site, wherein the target site comprises SEQ ID NO:4, for at least one sRNA molecule present in the plant, wherein expression of the gene of interest is downregulated only in tissues where the sRNA molecule is expressed.

25. The method of claim 24, wherein the gene of interest is an agronomic trait gene, an insect resistance gene, an herbicide tolerance gene, a non-coding RNA gene, or a selectable marker gene.

26. The method of claim 24, wherein the plant is a dicot plant selected from the group consisting of soybean, canola, cotton, and tobacco.

27. The method of claim 24, wherein the gene of interest is heterologous to the plant, and wherein the at least one sRNA molecule is an endogenous sRNA of the plant.

28. The method of claim 27, wherein the endogenous sRNA is expressed predominantly in seed tissue.

29. The method of claim 28, wherein the sRNA is SEQ ID NO:3.

\* \* \* \* \*